(12) United States Patent
Abt et al.

(10) Patent No.: US 12,214,160 B2
(45) Date of Patent: Feb. 4, 2025

(54) METHOD AND APPARATUS FOR SUBRETINAL INJECTION

(71) Applicant: Alcon Inc., Fribourg (CH)

(72) Inventors: Niels Alexander Abt, Winterthur (CH); Reto Grüebler, Greifensee (CH)

(73) Assignee: Alcon Inc., Fribourg (CH)

( * ) Notice: Subject to any disclaimer, the term of this patent is extended or adjusted under 35 U.S.C. 154(b) by 388 days.

(21) Appl. No.: 17/647,884

(22) Filed: Jan. 13, 2022

(65) Prior Publication Data

US 2022/0233768 A1    Jul. 28, 2022

Related U.S. Application Data

(60) Provisional application No. 63/141,051, filed on Jan. 25, 2021.

(51) Int. Cl.
| | |
|---|---|
| *A61M 5/158* | (2006.01) |
| *A61M 5/142* | (2006.01) |
| *A61M 5/168* | (2006.01) |
| *A61M 31/00* | (2006.01) |

(52) U.S. Cl.
CPC .......... *A61M 5/1582* (2013.01); *A61M 5/142* (2013.01); *A61M 5/16804* (2013.01); *A61M 31/00* (2013.01); *A61M 2005/14208* (2013.01); *A61M 2005/1585* (2013.01);
(Continued)

(58) Field of Classification Search
CPC ............ A61M 5/1582; A61M 25/0026; A61M 5/1407; A61M 5/142; A61M 31/00; A61M 2005/1585; A61M 2005/1588; A61M 2210/0612; A61M 2005/1586; A61M 2025/0286; A61M 2025/0293; A61M 2039/0261; A61M 2039/0297; A61M 5/16804; A61M 25/10; A61M 25/1002; A61M 2205/3306; A61M 2005/14208;
(Continued)

(56) References Cited

U.S. PATENT DOCUMENTS

| | | |
|---|---|---|
| 6,413,245 B1 | 7/2002 | Yaacobi |
| 6,986,900 B2 | 1/2006 | Yaacobi |
| 7,094,226 B2 | 8/2006 | Yaacobi |

(Continued)

FOREIGN PATENT DOCUMENTS

| | | | | |
|---|---|---|---|---|
| WO | 2004066871 A2 | 8/2004 | | |
| WO | WO-2014043586 A1 | * | 3/2014 | ......... A61B 1/00082 |
| WO | 2020031182 A1 | 2/2020 | | |

*Primary Examiner* — Tiffany Legette

(57) ABSTRACT

In certain embodiments, an apparatus is provided for performing a subretinal injection into a subretinal space between a retina and a retinal pigment epithelium of an eye. The apparatus includes an injection needle having a proximal end and a distal end, the distal end configured to be insertable into the subretinal space at a position on a surface of the retina. The apparatus includes a multi-lumen tubing having a distal end coupled to the proximal end of the injection needle and a proximal end coupled to a fluid control unit. The apparatus includes a stabilizer configured to immobilize the injection needle at the position on the surface of the retina. The fluid control unit has a plurality of fluid reservoirs containing a non-treatment solution, a treatment solution, and a working fluid which are injectable into the eye via separate lumens of the multi-lumen tubing.

7 Claims, 20 Drawing Sheets

(52) U.S. Cl.
CPC ............... *A61M 2005/1588* (2013.01); *A61M 2205/3306* (2013.01); *A61M 2210/0612* (2013.01)

(58) Field of Classification Search
CPC ............ A61F 9/0026; A61F 2009/0052; A61F 9/0017
See application file for complete search history.

(56) References Cited

U.S. PATENT DOCUMENTS

| | | | |
|---|---|---|---|
| 7,226,435 B2 | 6/2007 | Darnell | |
| 7,285,107 B1 | 10/2007 | Charles | |
| 7,951,060 B2* | 5/2011 | Larsen | A61N 5/1017 600/3 |
| 10,010,447 B2 | 7/2018 | Kashani | |
| 10,500,090 B2 | 12/2019 | Gunn et al. | |
| 10,993,614 B2 | 5/2021 | Charles | |
| 2004/0220559 A1* | 11/2004 | Kramer | A61B 18/02 606/22 |
| 2007/0038174 A1 | 2/2007 | Hopkins | |
| 2007/0060887 A1 | 3/2007 | Marsh | |
| 2008/0306440 A1* | 12/2008 | Hirszowicz | A61M 29/02 604/99.01 |
| 2010/0191176 A1* | 7/2010 | Ho | A61F 9/008 606/4 |
| 2017/0157350 A1* | 6/2017 | Van De Molengraaf | A61B 5/150656 |
| 2019/0105197 A1* | 4/2019 | LaBelle | A61M 5/32 |

* cited by examiner

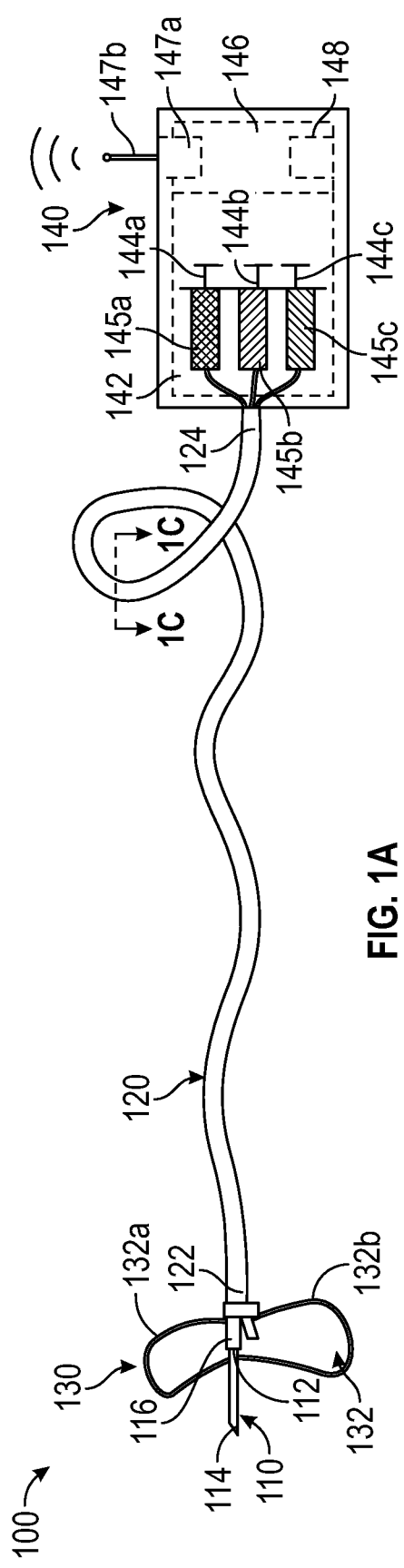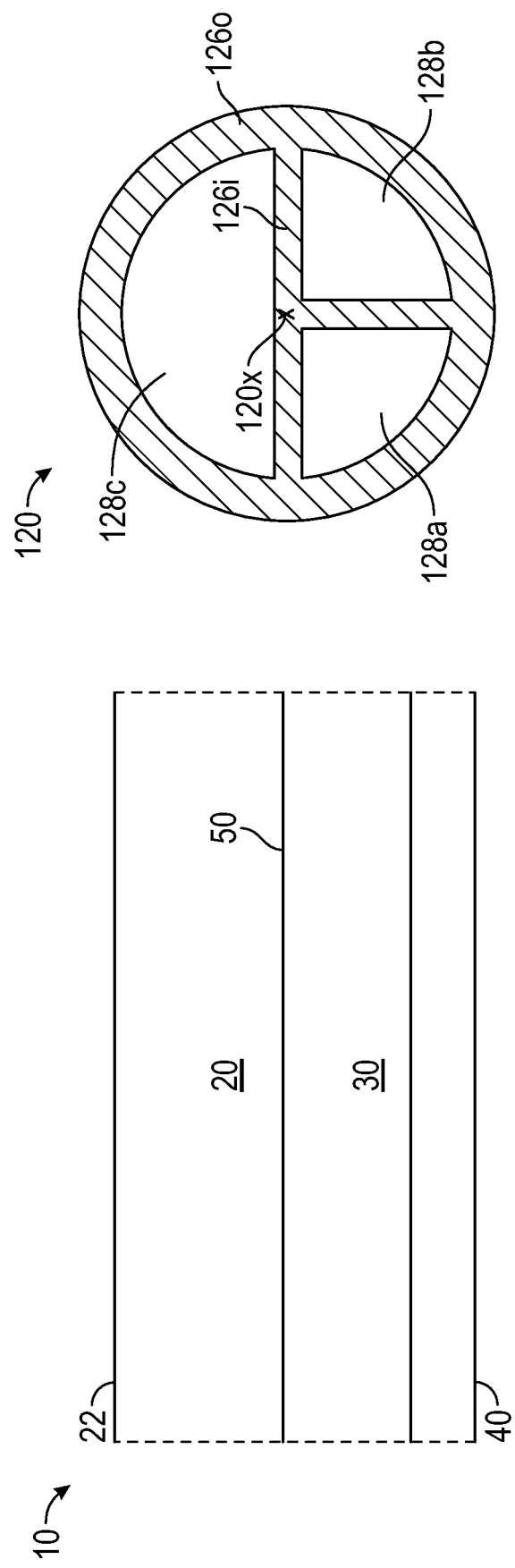
FIG. 1A
FIG. 1B
FIG. 1C

METHOD AND APPARATUS FOR SUBRETINAL INJECTION

PRIORITY CLAIM

This application claims the benefit of priority of U.S. Provisional Patent Application Ser. No. 63/141,051 titled "METHOD AND APPARATUS FOR SUBRETINAL INJECTION," filed on Jan. 25, 2021, whose inventors are Niels Alexander Abt and Reto Grüebler, which is hereby incorporated by reference in its entirety as though fully and completely set forth herein.

BACKGROUND

Field

Embodiments of the present disclosure generally relate to devices for ophthalmic treatment, and more particularly, to an apparatus and method for performing subretinal injection. Subretinal injection generally refers to injection of fluid or other therapeutic substances or stem cells into a subretinal space between a retina and a retinal pigment epithelium (RPE) of an eye.

Description of the Related Art

Certain diseases of the eye are treatable via injection into the subretinal space including, e.g., age-related macular degeneration (AMD) and retinal degenerative diseases and genetic defects. Typical practice requires at least two persons to administer the subretinal injection. For example, a lead surgeon may guide the injection instrument, e.g., a syringe/needle, and visually monitor the injection site, while a skilled surgical assistant pushes the fluid from the syringe and monitors the injection volume. Accordingly, typically, a first syringe is prepared with a small gauge needle and containing a non-treatment fluid, e.g., balanced salt solution (BSS). In the first step of the procedure, the first syringe is inserted through the retina into the subretinal space. While the surgeon handles the first syringe and visually monitors the injection site, the assistant manually injects the non-treatment fluid and monitors the injection volume. Next, the first syringe is removed from the eye.

A second syringe is prepared with a small gauge needle and containing a treatment fluid, e.g., including a therapeutic. In the second step of the procedure, the second syringe is inserted through the retina into the subretinal space at about the same location as the first syringe. While the surgeon handles the second syringe and visually monitors the injection site, the assistant manually injects the treatment fluid and monitors the injection volume. Consequently, there are many disadvantages with using a handheld injection instrument to manually control the injection in a two-step process. Some of these disadvantages are described below.

First, performing the injection with the injection instrument being handheld, as described above, can result in tearing of the retina. In particular, tearing of the retina can result from inadvertent movement of the syringe/needle due to external forces from outside the eye while the needle is inserted through the retina. The external forces may include inadvertent movements on the part of the surgeon during handling of the syringe or on the part of the assistant during manual control of the fluid injection.

Furthermore, manual control of the fluid injection, as described above, can have a number of additional disadvantages. Typically, manual control of the fluid injection involves manual depression of the plunger. For example, manual control of the fluid injection can result in incorrect injection volume, which can result in over- or under-dosing or excessive retinal stretch. In another example, manual control of the fluid injection can result in a high flow velocity into the subretinal space which can damage the retina or the RPE, e.g., causing rhegmatogenous-like retinal detachment with changes in retinal morphology or RPE atrophy. In yet another example, manual control of the fluid injection can result in a high shear force in the needle which can be detrimental to the biologic activity of various therapeutics, e.g., drugs, stem cells, viral vectors, carried by the injection fluid.

In addition, removing the first needle and inserting the second needle through the retina, as described above, can have further disadvantages. For example, making several insertions through the retina can contribute to retinal tearing. In another example, forming two different holes in the retina, one for each injection step, increases the potential for fluid to leak from the subretinal space.

Each of the problems described above can negatively impact the ophthalmic treatment being administered and/or carry an increased safety risk. Therefore, what is needed in the art are improved devices for ophthalmic treatment including an improved apparatus and method for subretinal injection.

SUMMARY

The present disclosure generally relates to devices for ophthalmic treatment, and more particularly, to an apparatus and method for performing subretinal injection.

In certain embodiments, an apparatus is provided for performing a subretinal injection into a subretinal space between a retina and a retinal pigment epithelium of an eye. The apparatus includes an injection needle having a proximal end and a distal end, the distal end configured to be insertable into the subretinal space at a position on a surface of the retina. The apparatus includes a multi-lumen tubing having a distal end coupled to the proximal end of the injection needle and a proximal end coupled to a fluid control unit, the multi-lumen tubing having a first lumen and a second lumen. The apparatus includes a stabilizer configured to immobilize the injection needle at the position on the surface of the retina. The fluid control unit has a first fluid reservoir containing a non-treatment solution and a second fluid reservoir containing a treatment solution. The fluid control unit is configured to inject the non-treatment solution from the first fluid reservoir to the subretinal space via the first lumen and to inject the treatment solution from the second fluid reservoir into the subretinal space via the second lumen.

In certain embodiments, a method is disclosed for performing a subretinal injection into a subretinal space between a retina and a retinal pigment epithelium of an eye. The method includes inserting a distal end of an injection needle into the subretinal space at a position on a surface of the retina, the injection needle having a proximal end coupled to a distal end of a multi-lumen tubing, the multi-lumen tubing having a proximal end coupled to a fluid control unit. The method includes immobilizing the injection needle at the position on the surface of the retina by applying a pressure or fluid through a first lumen of the multi-lumen tubing to extend a stabilizer beyond a distal end of the first lumen to contact the surface of the retina. The method includes injecting a non-treatment solution from the fluid control unit to the subretinal space via a second lumen of the multi-lumen tubing. The method includes injecting a treatment solution to the subretinal space via a third lumen of the multi-lumen tubing using the fluid control unit.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and may admit to other equally effective embodiments.

FIG. 1A is a schematic view of an exemplary injection apparatus for performing a subretinal injection, according to certain embodiments.

FIG. 1B is a transverse sectional view of a portion of an eye illustrating the retina and retinal pigment epithelium.

FIG. 1C is an enlarged side sectional view taken along the section line of FIG. 1A illustrating an exemplary multi-lumen tubing, according to certain embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Figure 1D:
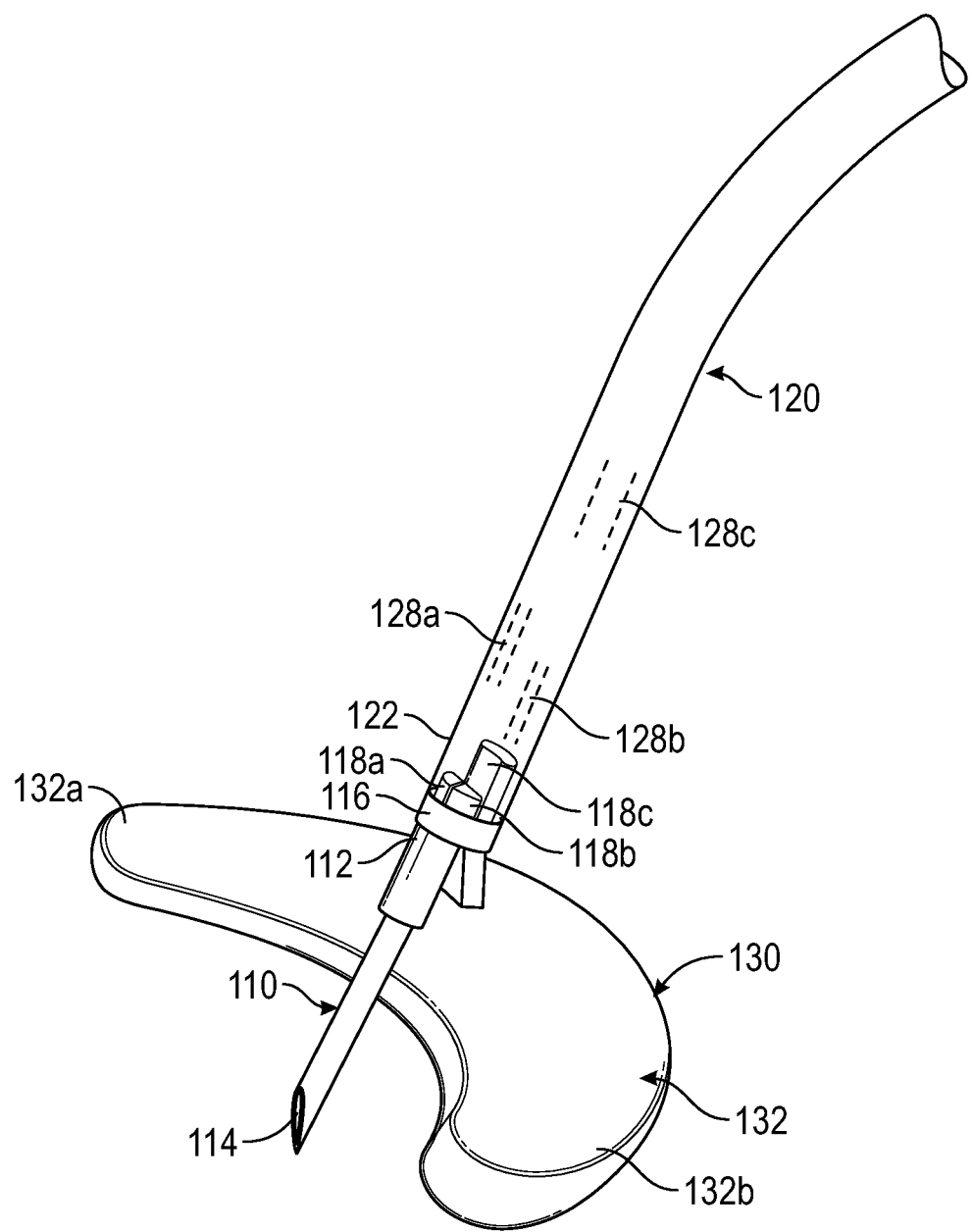
FIG. 1D is a top isometric view of a portion of the injection apparatus of FIG. 1A.

The present disclosure generally relates to devices for ophthalmic treatment, and more particularly, to an apparatus and method for performing subretinal injection.

Embodiments of the present disclosure describe an apparatus for performing a subretinal injection. In general, the apparatus includes an injection needle attached to a tubing which can be secured within the eye using a stabilizer such that the injection instrument does not need to be held throughout the entire procedure. This provides decoupling of the injection needle from undesirable movements that would otherwise occur when the injection instrument is handheld. Furthermore, the tubing of the apparatus is coupled to a fluid pump outside the eye in order to automate the actual fluid injection process. Automated control of fluid injection can improve control over injection volumes as well as improve control of important flow related parameters of the injection fluid compared to manual control of fluid injection. Additionally, the tubing of the apparatus is a multi-lumen tubing which provides a plurality of parallel flow paths from separate fluid reservoirs to the injection needle so that the injection can be performed using only one needle. Having to insert only one needle through the retina can reduce damage to the retina which could otherwise occur from repeated piercing of the retina.

FIG. 1A is a schematic view of an exemplary injection apparatus 100 for performing a subretinal injection. FIG. 1B is a transverse sectional view of a portion of an eye 10. FIGS. 1A-1B are, therefore, described together herein for clarity. In particular, the injection apparatus 100 is configured to perform a subretinal injection into a subretinal space 50 between a retina 20 and a retinal pigment epithelium (RPE) 30 of the eye 10 (FIG. 1B). As illustrated in FIG. 1A, the injection apparatus 100 generally includes an injection needle 110, a multi-lumen tubing 120, a stabilizer 130, and a fluid control unit 140.

Referring to FIG. 1A, the injection needle 110 has a proximal end 112 and a distal end 114. The distal end 114 of the injection needle 110 is configured to be inserted into the subretinal space 50 at a target position on a surface 22 of the retina 20 (FIG. 1B). The injection needle 110 includes a connector piece 116 (described in more detail below) at the proximal end 112 that connects the injection needle 110 to the multi-lumen tubing 120. The multi-lumen tubing 120 has a distal end 122 attached to the proximal end 112 of the injection needle 110 through the connector piece 116 and a proximal end 124 attached to the fluid control unit 140.

FIG. 1C is an enlarged side sectional view taken along the section line of FIG. 1A illustrating an exemplary multi-lumen tubing 120. The multi-lumen tubing 120 includes an outer wall 126o surrounding three lumens 128a, 128b, and 128c. Although FIG. 1C shows three lumens, more or less lumens can be used (e.g., two or more lumens, from two to four lumens, two lumens, or four lumens). The lumens 128a-c are divided by inner walls 126i intersecting the outer wall 126o. The lumens 128a-c are radially surrounding a center longitudinal axis 120x of the multi-lumen tubing 120. In the embodiments of FIG. 1C, one or more of the lumens 128a-c have different sizes. For example, each of the lumens 128a, 128b extend one-quarter of the way around the multi-lumen tubing 120 in a circumferential direction. On the other hand, the lumen 128c extends halfway around the multi-lumen tubing 120 in the circumferential direction. Therefore, in the embodiments of FIG. 1C, a volume of the lumen 128c may be twice as much as a volume of each of the lumens 128a, 128b. In some other embodiments, each of the lumens 128a-c has the same size. In certain embodiments, the multi-lumen tubing 120 is formed from a polymer such as silicone, polyurethane (PUR), polyamide (PA) (e.g., nylon), polyethylene (PE), polyether block amide (PEBA), polytetrafluoroethylene (PTFE), polyimide (PI), fluorinated ethylene propylene (FEP), perfluoroalkoxy alkane (PFA), polyether ether ketone (PEEK), liquid crystal polymer (LCP), ethylene tetrafluoroethylene (ETFE), a terpolymer of tetrafluoroethylene, hexafluoropropylene and vinylidene fluoride (THV), a thermoplastic elastomer (TPE), or combinations thereof. In some embodiments, the injection needle 110 and the multi-lumen tubing 120 are formed from the same or different materials.

The fluid control unit 140 includes a fluid pump 142 for driving flow through the multi-lumen tubing 120. Although FIG. 1A shows a syringe pump, the fluid pump 142 can include at least one of a Vernier Flow Control (VFC) pump or another type of pressure control pump, a volume control pump, a variable volume control pump, a peristaltic pump, a lever-actuated pump, a valve-actuated pump, or a venturi pump. The fluid control unit 140 also includes three fluid reservoirs 144a, 144b, and 144c for storing a plurality of fluids 145a-c. Although FIG. 1A shows three fluid reservoirs, more or less fluid reservoirs can be used. Referring to FIG. 1A, each of the fluid reservoirs 144a-c is a syringe configured to be actuated by the syringe pump. In certain embodiments, the plurality of fluids 145a-c include a non-treatment solution 145a, a treatment solution 145b, and a working fluid 145c.

In operation, the fluid pump 142 is configured to drive flow of each of the plurality of fluids 145a-c from the fluid reservoirs 144a-c, respectively, through the lumens 128a-c, respectively, of the multi-lumen tubing 120 (FIG. 1C). As further described below, when the injection needle 110 is first inserted into the retina 20, initially working fluid 145c is configured to flow through the port 118c of the connector piece 116 (FIG. 1D) to extend the stabilizer 130 and stabilize the injection needle 110. Then, the non-treatment solution 145a and the treatment solution 145b are configured to flow through the ports 118a, 118b, respectively, of the connector piece 116 (FIG. 1D) in order to separately inject each of the fluids 145a, 145b into the subretinal space 50 (FIG. 1B). Note that FIG. 1A illustrates stabilizer 130 in an extended state. Additional details regarding the operations of stabilizer 130 are provided with respect to FIG. 1D.

In some embodiments, the non-treatment solution 145a includes an ophthalmic irrigation solution having physiological pH and osmotic pressure (e.g., BSS). In some embodiments, the treatment solution 145b includes a therapeutic substance for treating the eye 10 (e.g., anti-VEGF, tissue plasminogen activator (tPA), stem cells, viral vectors for gene therapy, other drugs, or combinations thereof). In some embodiments, the working fluid 145c includes a fluid for extending the stabilizer 130 (e.g., perfluorocarbon liquid (PFCL), BSS, saline, air, $N_2$, other liquids or gases, or combinations thereof).

The fluid control unit 140 includes a controller 146 for controlling operation of the fluid pump 142. In certain embodiments, the controller 146 includes a wireless receiver 147a having an antenna 147b for receiving instructions wirelessly from a control console. The fluid control unit 140 includes a power supply 148 for powering the fluid pump 142 and the controller 146. In some embodiments, the power supply 148 includes at least one of a battery, one or more spring, or a gas container. In some other embodiments, power is provided by at least one of gravity force or manual actuation. In some other embodiments, the fluid control unit 140 also includes a plurality of valves for regulating fluid flow from the fluid reservoirs 144a-c.

FIG. 1D is top isometric view of a portion of the injection apparatus 100 of FIG. 1A. Referring to FIG. 1D, the connector piece 116 has three ports 118a, 118b, 118c corresponding to and disposed within the distal ends of the lumens 128a-c, respectively, of the multi-lumen tubing 120. The two separate ports 118a, 118b of the connector piece 116 merge together toward the distal end 114 of the injection needle 110. The port 118c, on the other hand, is separate from each of the ports 118a, 118b and fluidly isolated therefrom. The port 118c is fluidly coupled to the stabilizer 130 as shown.

Referring to FIGS. 1A and 1D, the stabilizer 130 is shown in the extended or activated position where the stabilizer 130 extends from the port 118c of the connector piece 116. In the extended position, the stabilizer 130 stabilizes the injection needle 110 and controls the location of injection of the non-treatment solution 145a in order to help force the location of the bleb which is described in more detail below with regard to FIGS. 4 and 9A-9C. In the embodiments of FIGS. 1A and 1D, the stabilizer 130 is a balloon 132, or bag, having a pair of wings 132a, 132b. In some other embodiments, the balloon 132 can have any suitable shape including without limitation, round, oval, or polygonal. The balloon 132 may be formed from plastic, metal, polymer, nitinol, or combinations thereof.

Figure 2A:
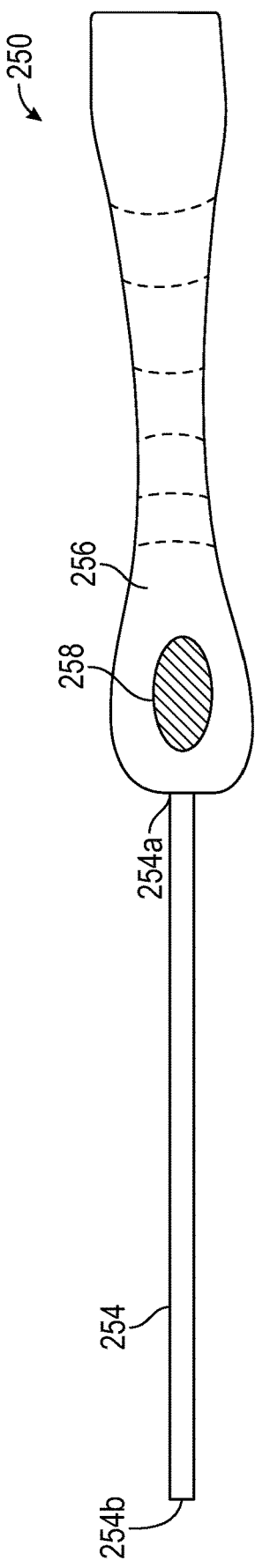
FIG. 2A is a schematic view of an exemplary inserter device, which may be used with the injection apparatus described herein, according to certain embodiments.
Figure 2B:
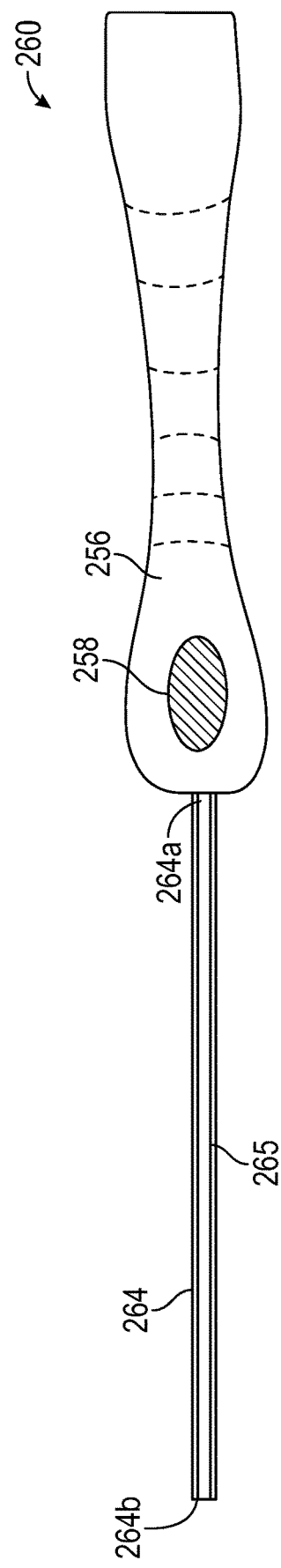
FIG. 2B is a schematic view of another exemplary inserter device, which may be used with the injection apparatus described herein, according to certain embodiments.
Figure 2C:
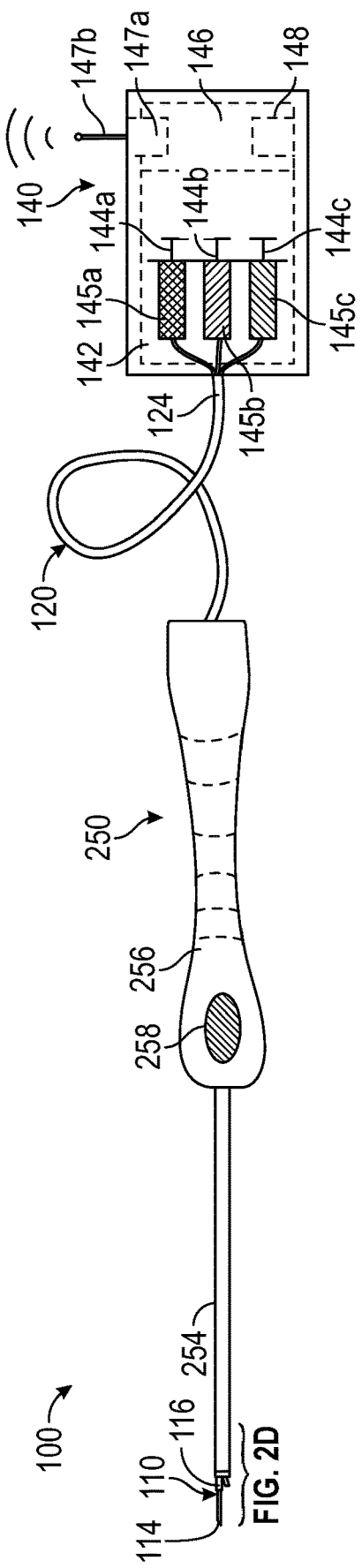
FIG. 2C is a schematic view of the injection apparatus of FIG. 1A illustrating an exemplary inserter device combined therewith, according to certain embodiments.
Figure 2D:
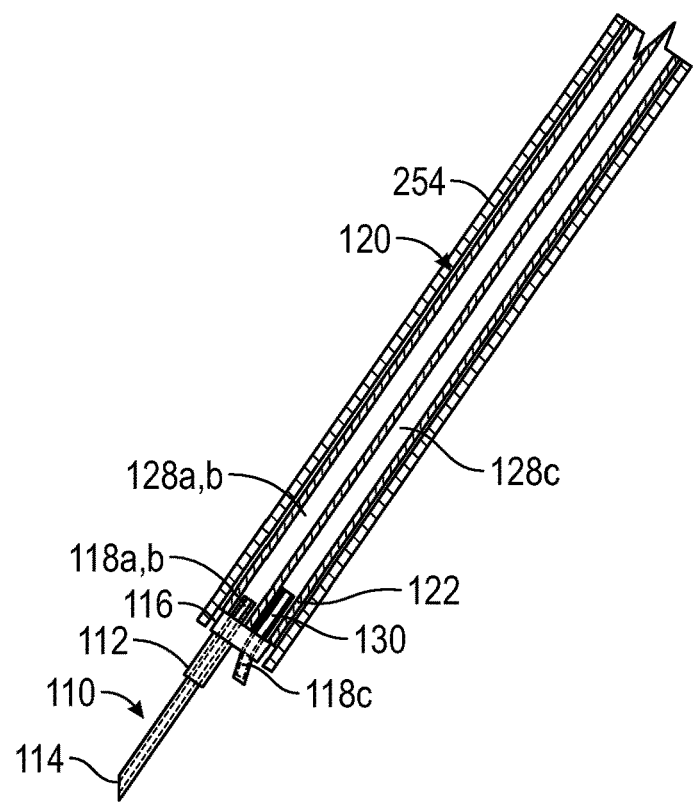
FIG. 2D is an enlarged side sectional view of a portion of FIG. 2C illustrating an exemplary injection needle, used in connection with the injection apparatus described herein, according to certain embodiments.

Before the stabilizer 130 is in the extended position as shown in FIGS. 1A and 1D, the stabilizer 130 is disposed within the port 118c of the connector piece 116 as shown in FIG. 2D and described in detail below. In certain embodiments, to actuate the stabilizer 130 to the extended position, the working fluid 145c (e.g., PFCL) is injected from the fluid reservoir 144c of the fluid control unit 140 (FIG. 1A) through the lumen 128c to fill the balloon 132 with PFCL. In the extended position, the wings 132a, 132b of the balloon 132 extend substantially along an axis perpendicular to the center longitudinal axis 120x of the multi-lumen tubing 120. In some embodiments, in the extended position, the balloon 132 has a flattened profile. For example, in some embodiments, a width of the balloon 132 measured parallel to the surface 22 of the retina 20 is greater (e.g. at least 2× greater, at least 5× greater, or at least 10× greater) than a height of the balloon 132 measured orthogonal to the surface 22. Beneficially, the flattened profile increases the contact surface area between the balloon 132 and the surface 22. In certain embodiments, the balloon 132 is held in place primarily due to the weight of the working fluid 145c in the balloon 132. Note that FIGS. 1A and 1D show only one example of a stabilizer. Additional examples, which may operate differently are described further in relation to FIGS. 15-17.

In the extended position, the stabilizer 130 is configured to immobilize the injection needle 110 at a target position on the surface 22 of the retina 20, which reduces the likelihood of the injection needle 110 being removed from the subretinal space 50 during the treatment due to light inadvertent forces. As used herein, immobilizing the injection needle 110 generally refers to limiting movement of the injection needle 110 relative to the retina 20 in order to maintain the injection needle 110 at the target position on the surface 22 of the retina 20 throughout the treatment. That is to say that immobilizing the injection needle 110 does not refer to limiting the injection needle 110 to zero or no movement. Instead, the injection needle 110 should still retain some limited degree of freedom while being maintained at the target position so that light and/or inadvertent forces can be safely applied without tearing the retina 20. In addition, the injection needle 110 should still be removable from the retina 20 even in the extended position in the event that enough force is applied to the injection needle 110. Allowing the injection needle 110 to be removed in response to a large enough pull force prevents harm the eye 10 or major tearing. Additional details regarding the stabilizer 130 and its operations are provided with respect to FIGS. 5-12.

FIG. 2A is a schematic view of an exemplary inserter device 250, which may be used with the injection apparatus 100 described herein. In general, the inserter device 250 is configured to be releasably coupled to the injection needle 110 to provide a rigid structure for inserting the injection needle 110 into the eye 10 and further into the subretinal space 50. The inserter device 250 includes a cannula 254 which is a portion of the inserter device 250 directly engaging the injection needle 110 and which is insertable into the eye 10. The cannula 254 has a bore for surrounding the multi-lumen tubing 120. In the embodiments of FIG. 2A, the cannula 254 has an enclosed bore extending longitudinally from a proximal end 254a to a distal end 254b thereof.

The cannula 254 extends from a body 256 which is a portion of the inserter device 250 configured to be gripped and handled by the surgeon or surgical assistant. The body 256 has an injection needle release knob 258 for releasing the injection needle 110 from the cannula 254 when the injection needle 110 is properly positioned and immobilized within the eye 10. It is contemplated that the release knob 258 may function in several different ways. For example, the release knob 258 may be a slide which moves a release mechanism to disengage the cannula 254 from the connector piece 116 allowing the cannula 254 to be retracted away from the injection needle 110. In certain embodiments, the release mechanism includes a pair of inner and outer tubes enclosing the connector piece 116, the inner and outer tubes having respective openings such that turning the inner tube to align the openings releases the injection needle 110. In certain other embodiments, the release mechanism includes a cone tube which moves inside a ring surrounding and holding the connector piece 116 such that inserting the cone tube enlarges the inner diameter of the ring to release the injection needle 110. In certain other embodiments, the release mechanism includes two half-shells enclosing the connector piece 116 and held together by a ring such that moving the ring releases the injection needle 110. Alternatively, the cannula 254 may be spring-loaded such that pressing the release knob 258 causes the cannula 254 to be retracted away from the injection needle 110. Alternatively, utilizing the U-shaped cannula 264 (described in more detail below) the release knob 258 may push the cannula 264 to one side thereby disengaging the cannula 264 from the connector piece 116 through a slit 265 formed along a length of the cannula 264. In the embodiments of FIG. 2A, the inserter device 250 is configured to remain coupled to the multi-lumen tubing 120 outside the eye 10, namely because the enclosed bore prevents the cannula 254 from being removed from around the multi-lumen tubing 120. Note that FIG. 2A shows only one example of an inserter device. An additional example, which may operate differently is described further in relation to FIG. 2B.

FIG. 2B is a schematic view of another exemplary inserter device 260, which may be used with the injection apparatus 100 described herein. Referring to FIG. 2B, the inserter device 260 is constructed and arranged similarly to the inserter device 250 of FIG. 2A, except where noted, and corresponding description thereof may be incorporated herein without limitation. In one or more embodiments, the cannula 264 has a slit 265 extending longitudinally from a proximal end 264a to a distal end 264b thereof. In some embodiments, the cannula 264 has a U-shape in cross-section. In some embodiments, the slit 265 has a minimum width greater than an outer diameter of the multi-lumen tubing 120. In such embodiments, the inserter device 260 is configured to be decoupled from the multi-lumen tubing 120 outside the eye 10 by sliding the multi-lumen tubing 120 through the slit 265.

FIG. 2C is a schematic view of the injection apparatus 100 of FIG. 1A illustrating an exemplary inserter device 250 combined therewith. FIG. 2D is an enlarged side sectional view of a portion of FIG. 2C illustrating an exemplary injection needle 110, used in connection with the injection apparatus 100 described herein. FIGS. 2C-2D are, therefore, described together herein for clarity. The injection apparatus 100 is shown in a configuration ready to start the subretinal injection procedure. For example, the inserter device 250 is coupled to the injection needle 110, and the cannula 254 of the inserter device 250 is surrounding the multi-lumen tubing 120. Furthermore, the stabilizer 130 is in the retracted position being disposed inside the port 118c of the connector piece 116 which is disposed within the distal end 254a of the cannula 254. FIG. 2D illustrates a straight injection needle 110. In other words, the injection needle 110 extends from the proximal end 112 of the injection needle 110 to the distal end 114 of the injection needle 110 at a constant angle which is substantially parallel to the center longitudinal axis 120x of the multi-lumen tubing 120. In certain embodiments, as shown in FIG. 2D, the cannula 254 of the inserter device 250 extends beyond the distal end 122 of the multi-lumen tubing 120 and surrounds the connector piece 116 of the injection needle 110. In some embodiments of FIG. 2D, the cannula 254 has an inner diameter corresponding to an outer diameter of the connector piece 116.

Figure 3:
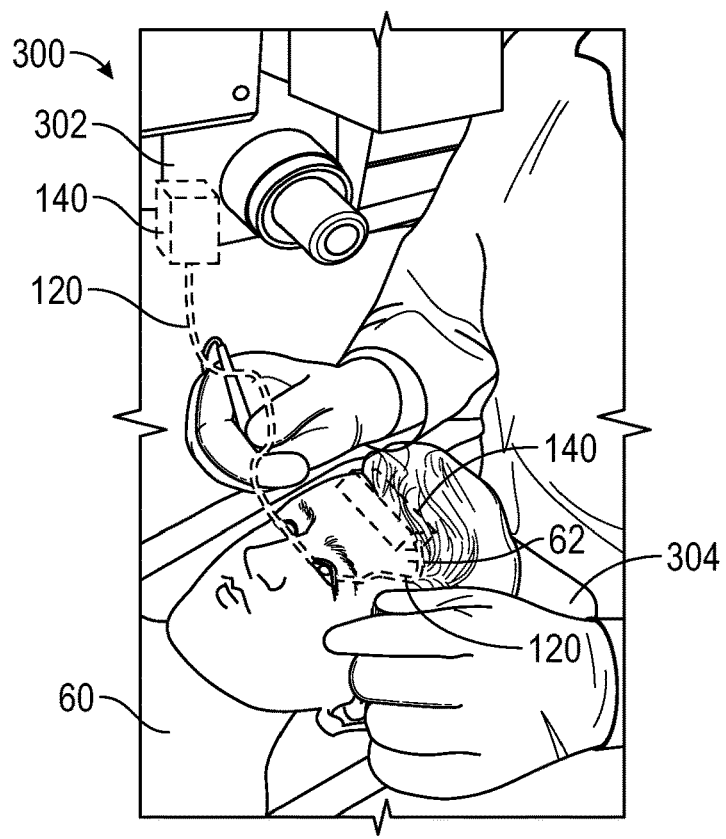
FIG. 3 is an isometric view of an exemplary injection apparatus for performing a subretinal injection used during operation, according to certain embodiments.

FIG. 3 is an isometric view of an exemplary injection apparatus 300 for performing a subretinal injection. Referring to FIG. 3, the injection apparatus 300 is used in connection with a surgical microscope 302 and an operating table 304. In certain optional embodiments illustrated in FIG. 3, the fluid control unit 140 is attached to the surgical microscope 302. In certain other optional embodiments illustrated in FIG. 3, the fluid control unit 140 is attached to and/or rested on a forehead 62 of a patient 60 lying on the operating table 304. There are several advantages, described below, associated with positioning the fluid control unit 140 on the surgical microscope 302 or the forehead 62 as shown in FIG. 3.

A first advantage is that attaching the fluid control unit 140 to a fixed object reduces the likelihood of external forces being applied to the multi-lumen tubing 120, which reduces the likelihood of the injection needle 110 coming out or tearing the retina 20. In other words, attaching the fluid control unit 140 to a fixed object helps achieve decoupling of the fluid control unit 140 from objects that move which reduces the impact of external forces.

Another advantage is that by positioning the fluid control unit 140 in close proximity to the eye 10 (e.g., on the surgical microscope 302 or the forehead 62) as compared to some other embodiments where the fluid control unit 140 is positioned at a further distance from the eye 10, a total relative length of the multi-lumen tubing 120 is reduced. This thereby reduces a dead volume of each of the plurality of fluids 145a-c in the multi-lumen tubing 120 between the fluid reservoirs 144a-c and the eye 10. Because the cost of therapeutic treatment fluids is often very high, reducing fluid waste due to the dead volume, in the multi-lumen tubing 120 for example, can result in significant cost savings. It is also contemplated that reducing the distance between the fluid control unit 140 and the eye 10 reduces the elasticity of the system providing more rigid fluid control.

In some other embodiments, the dead volume in the multi-lumen tubing 120 can be reduced by using a micro-lumen tubing which has a reduced outer diameter and reduced cross-sectional flow area relative to standard tubing. For example, it is contemplated that micro-lumen tubing may have an outer diameter of about 0.3 mm or less, whereas standard tubing has an outer diameter of about 0.4 mm.

In some other embodiments, the dead volume in the multi-lumen tubing 120 can be reduced by front loading each of the plurality of fluids 145a-c into the multi-lumen tubing 120. In such embodiments, the injection needle 110 is configured to be removed from the distal end 122 of the multi-lumen tubing 120 (FIG. 2D) so that each of the plurality of fluids 145a-c can be loaded directly into a distal end 122 of one of the lumens 128a-c. In other words, the plurality of fluids 145a-c are stored within a portion of the multi-lumen tubing 120 instead of within the fluid reservoirs 144a-c. In such embodiments, the dead volume in the multi-lumen tubing 120 upstream of the plurality of fluids 145a-c (i.e., between the fluid reservoirs 144a-c and the plurality of fluids 145a-c, respectively) can be filled with a relatively low cost chaser fluid (e.g., air, $N_2$, BSS, saline, other liquids or gases, or combinations thereof). In such embodiments, the chaser fluid is pressurized by the fluid pump 142, which in turn pressurizes the fluid stored in the multi-lumen tubing 120. In some embodiments, the lumen 128b is front-loaded with the treatment solution 145b, which is relatively more costly, while the lumens 128a, 128c receive the non-treatment solution 145a and the working fluid 145c, respectively, from the fluid reservoirs 144a, 144c, respectively.

Figure 4:
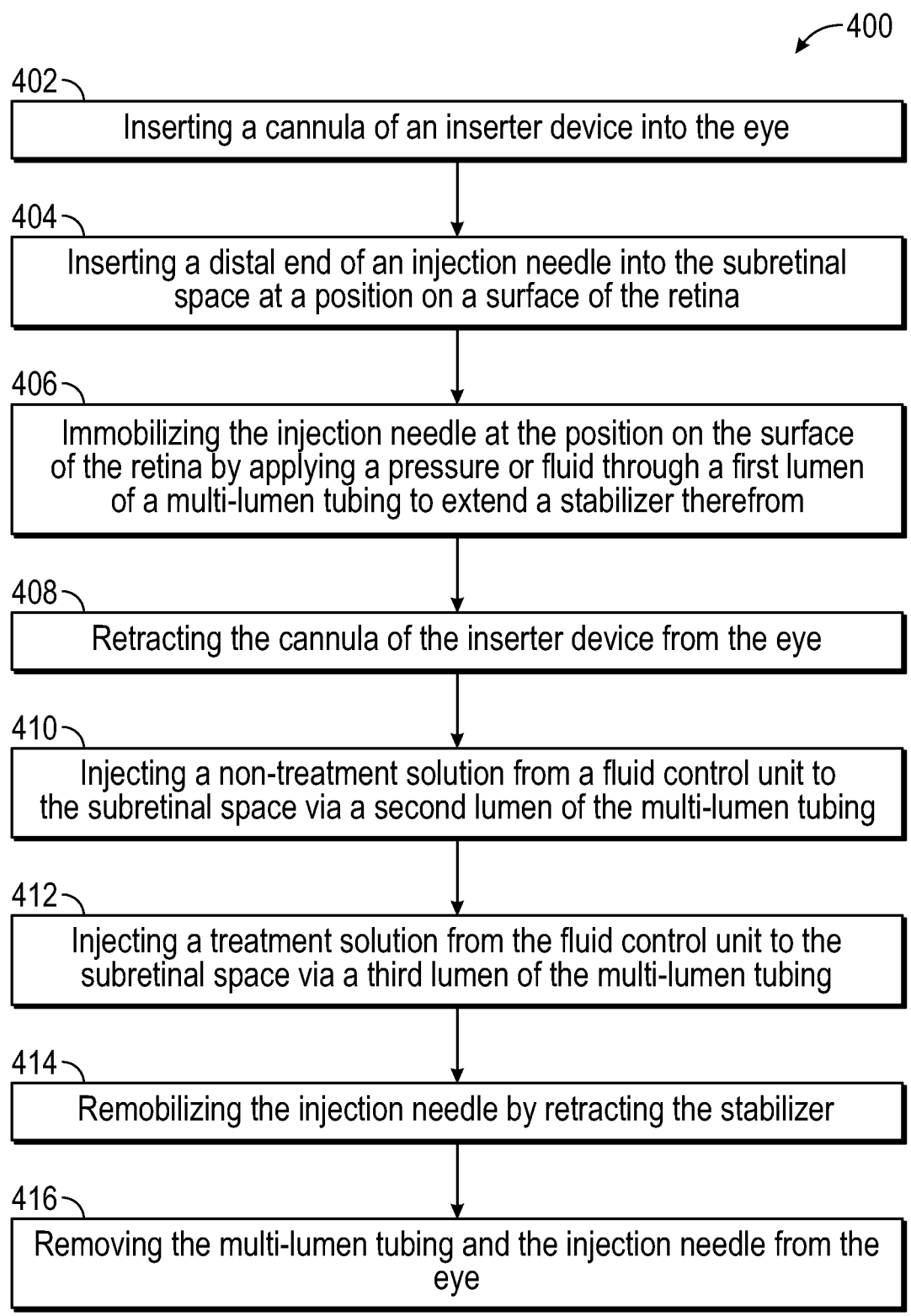
FIG. 4 is a diagram illustrating a method of performing a subretinal injection, according to certain embodiments.
Figure 5A:
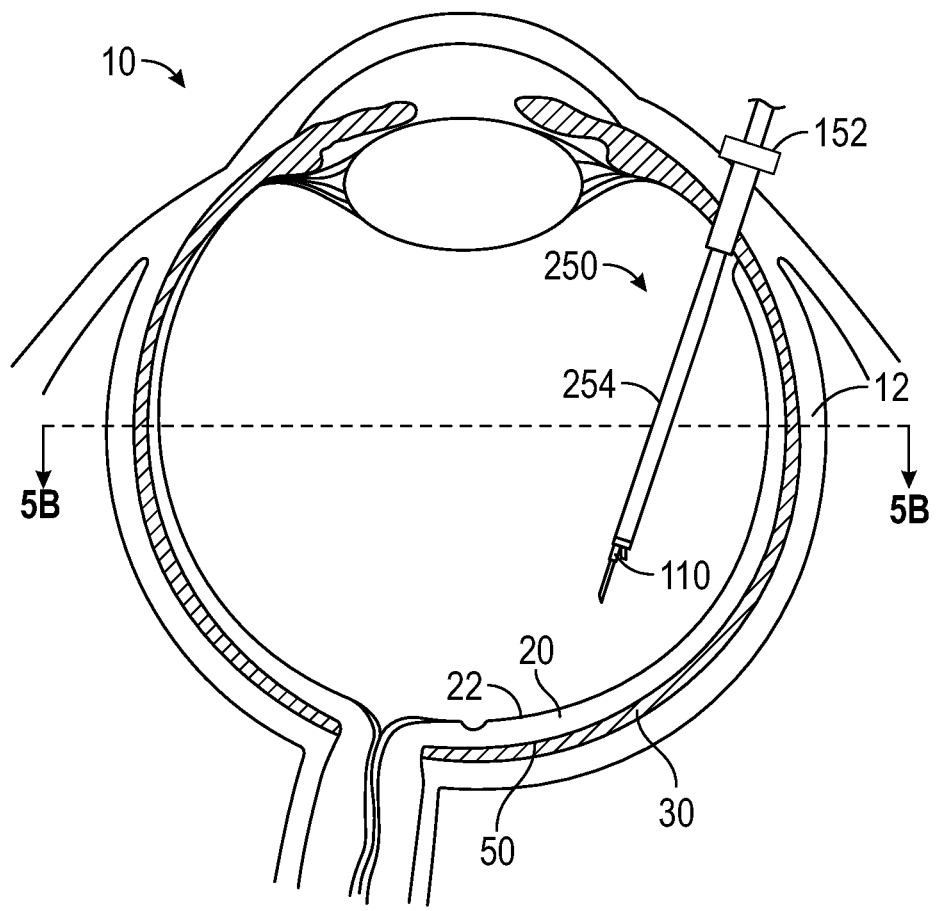
FIGS. 5A, 6A, 7A, 8A, 9A, 10A, 11A, and 12A are transverse sectional views of an eye at different operations of the method of FIG. 4, according to certain embodiments.
Figure 5B:
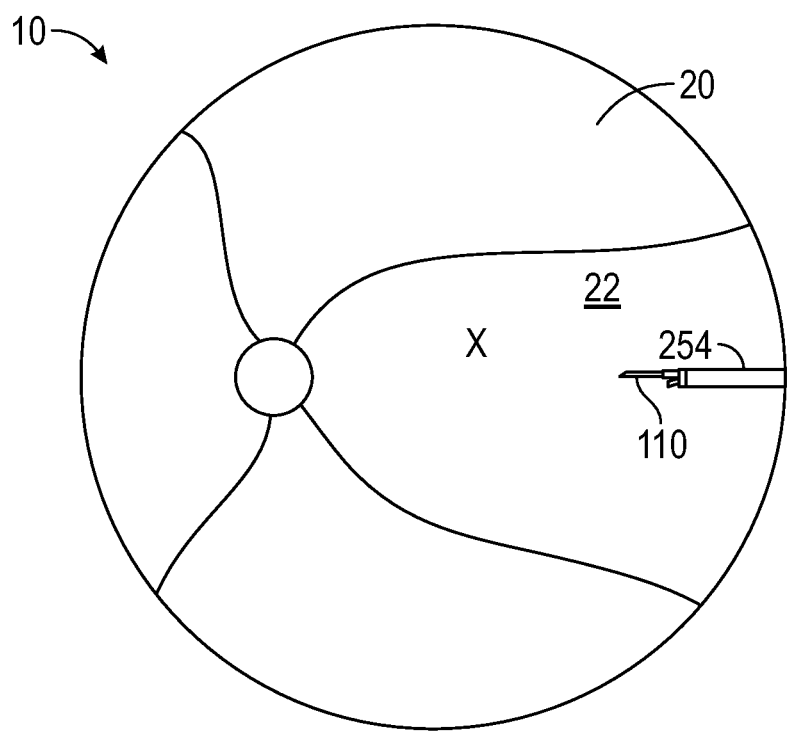
FIGS. 5B, 6B, 7B, 8B, 9B, 10B, 11B, and 12B are sectional views taken along section lines of 5A, 6A, 7A, 8A, 9A, 10A, 11A, and 12A, respectively, according to certain embodiments.

FIG. 4 is a diagram illustrating a method 400 of performing a subretinal injection using the injection apparatus 100 described herein. In preparation for the subretinal injection, the sclera 12 is incised using a trocar cannula which consists of a valved cannula 152 (FIG. 5A) and a trocar. Typically, a pre-packaged trocar cannula having a hub at a proximal end is inserted into the eye 10 to the point that a bottom surface of the hub contacts the sclera 12. Then, the trocar is removed from the eye 10 leaving the valved cannula 152 in place as shown in FIG. 5A. Although not shown, in FIGS. 5A-12A the bottom surface of the hub of the valved cannula 152 may be parallel to or flush with the surface of the eye 10. At operation 402, the cannula 254 of the inserter device 250 is inserted into the eye 10 through the valved cannula 152 (FIGS. 5A-5B).

Figure 6A:
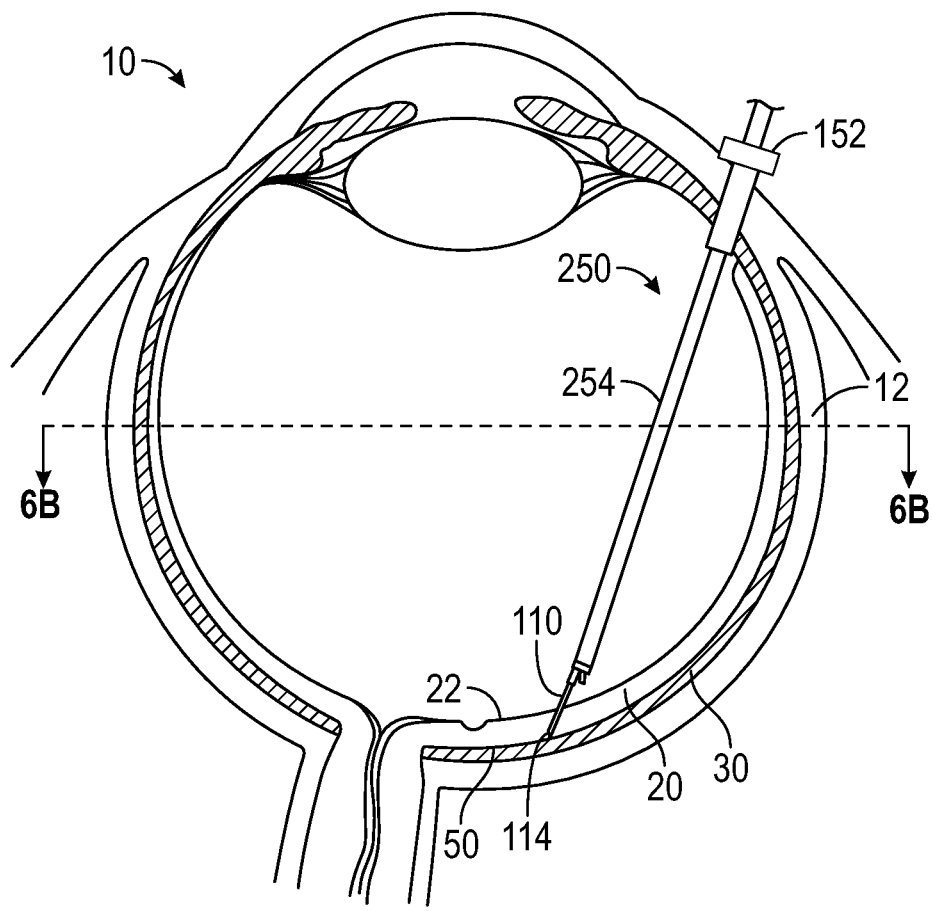
Figure 6B:
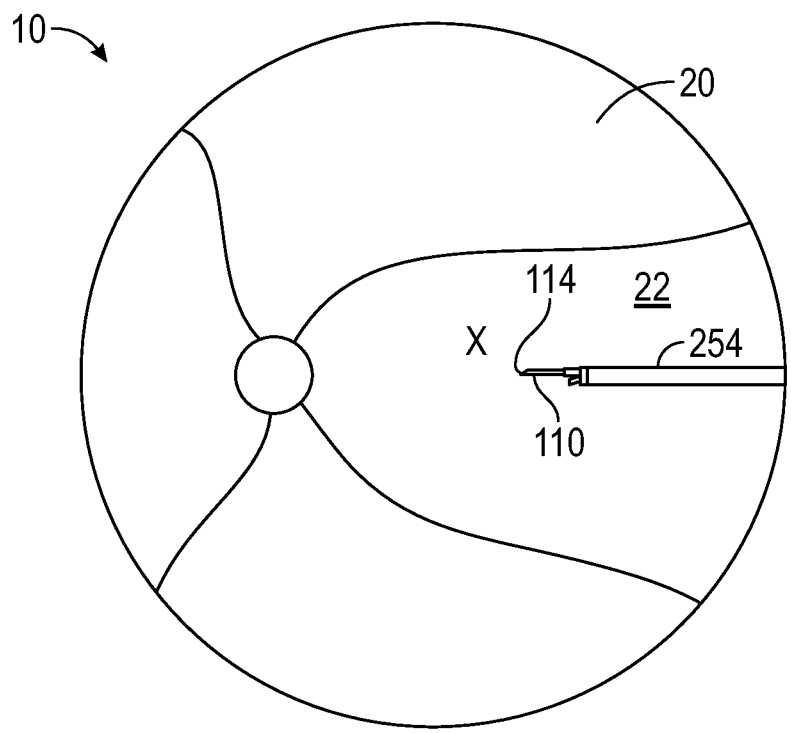
Figure 7A:
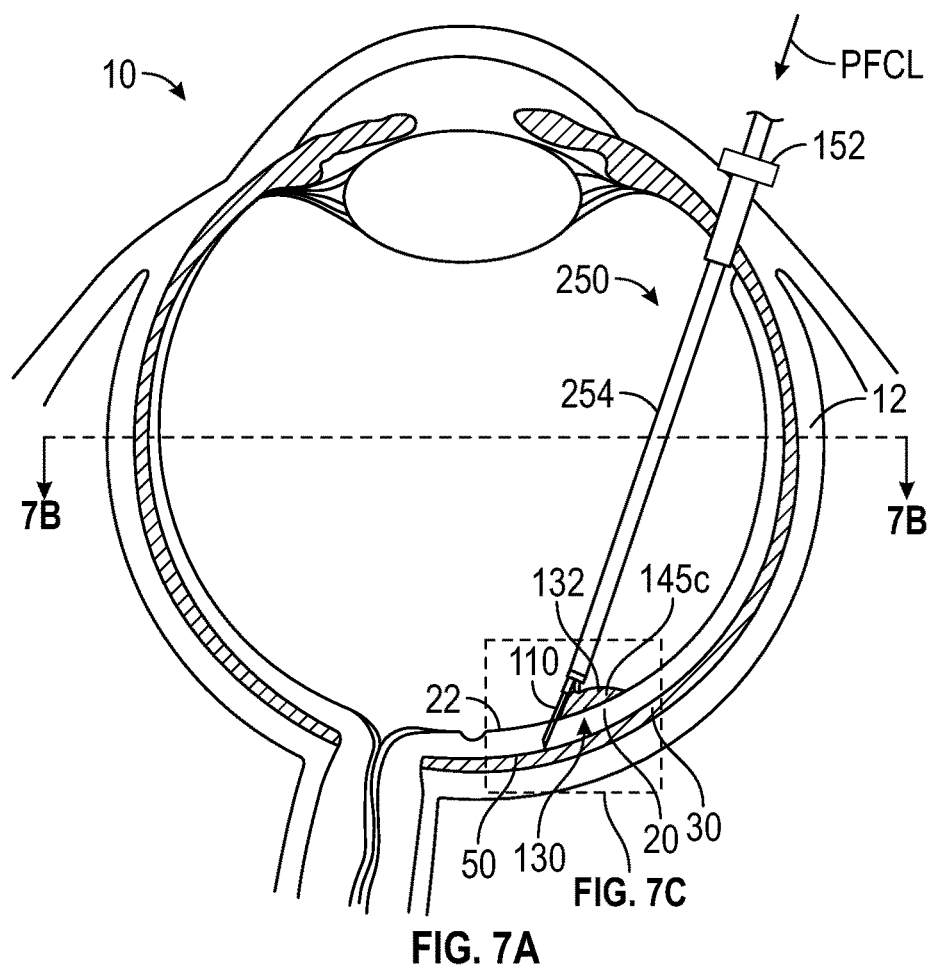
Figure 7B:
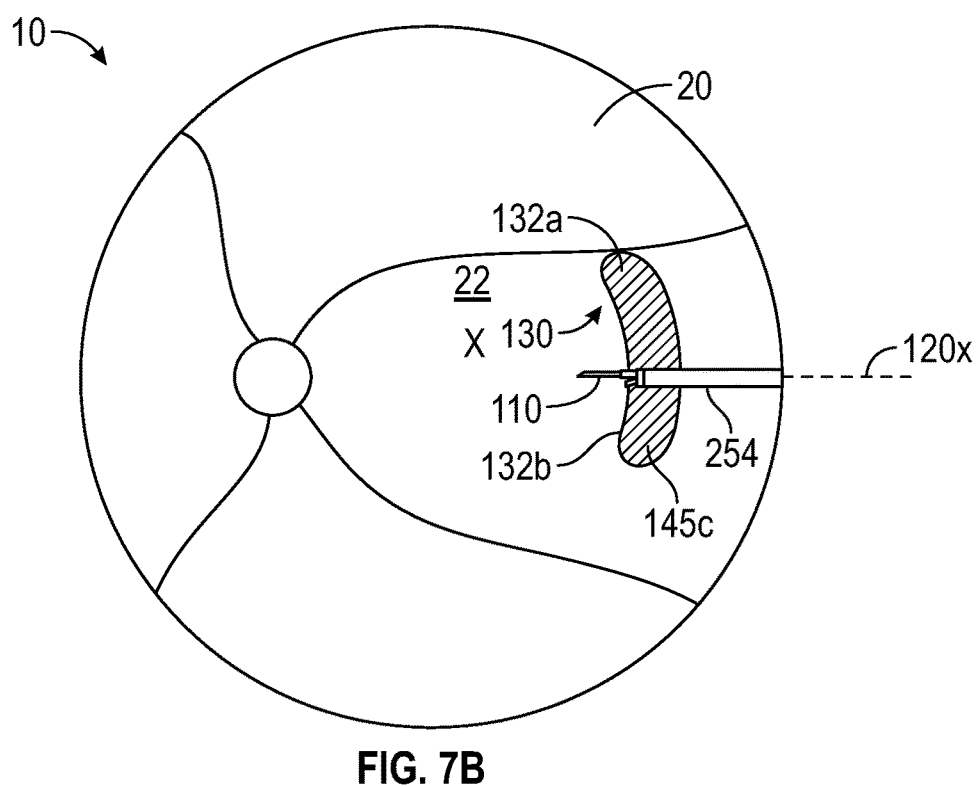
Figure 7C:
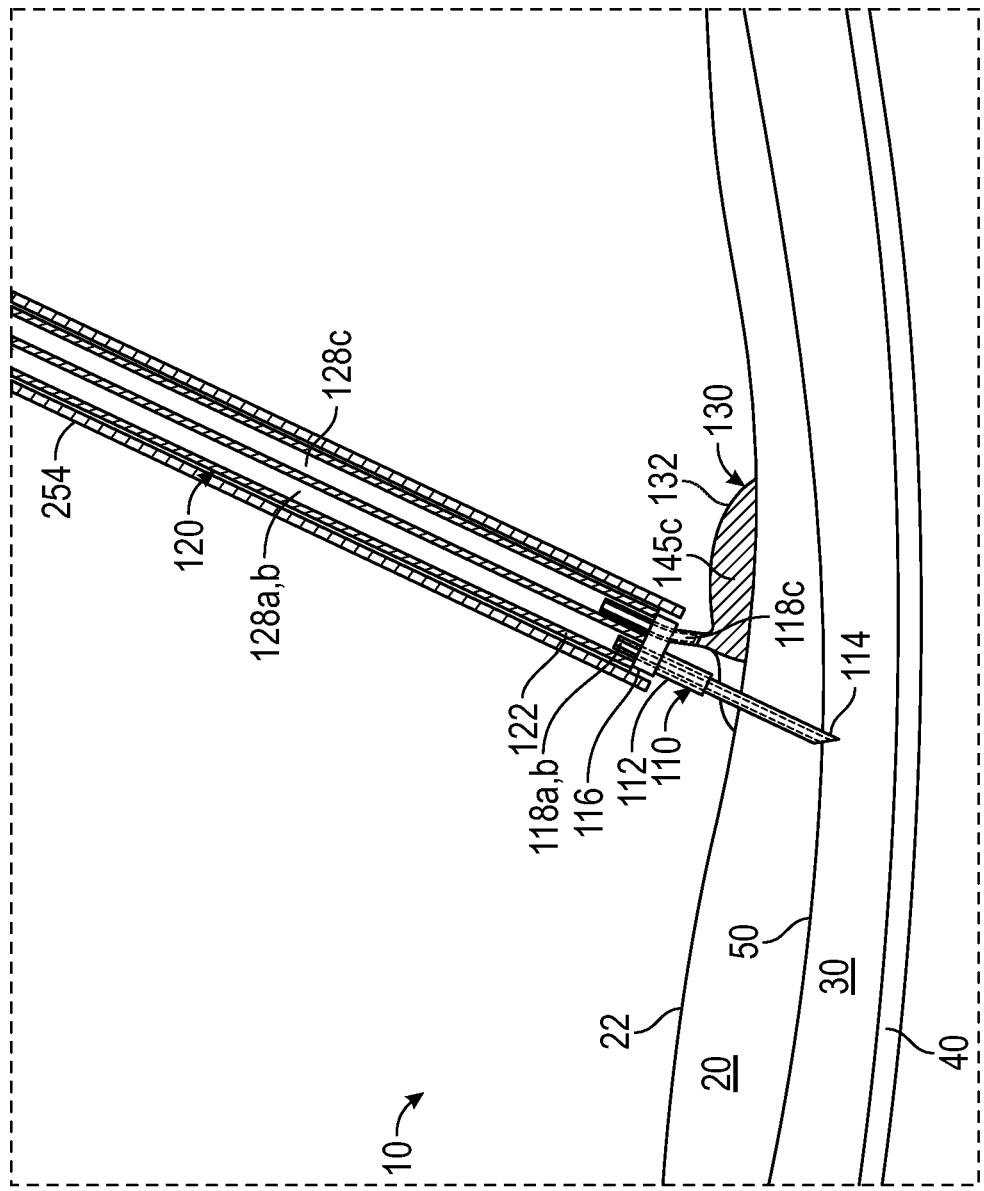
FIG. 7C is an enlarged sectional view of a portion of FIG. 7A illustrating an exemplary stabilizer, which may be used with the injection apparatus described herein, according to certain embodiments.

At operation 404, the distal end 114 of the injection needle 110 is inserted into the subretinal space 50 at a target position on the surface 22 of the retina 20 (FIGS. 6A-6B). In some embodiments, the depth of the injection needle 110 is controlled visually. For example, in some embodiments, optical coherence tomography (OCT) imaging data can be utilized during surgery to provide visual confirmation that the distal end 114 of the injection needle 110 is disposed within the proper layer of the eye 10, namely in the subretinal space 50. In certain embodiments, the connector piece 116 functions as an end stop to prevent the injection needle 110 from being inserted too far into the eye 10 (e.g., through the RPE 30 or the Bruch's membrane 40), which can damage the eye 10. In some embodiments, the length of the injection needle 110 measured from the connector piece 116 to the distal end 114 thereof is selected so that the distal end 114 is correctly positioned between the retina 20 and the RPE 30 when the connector piece 116 is in contact with the surface 22 of the retina 20. In some embodiments, the length of the injection needle 110 may be selected based on a pre-operative determination of the thickness of the retina 20.

Figure 13A:
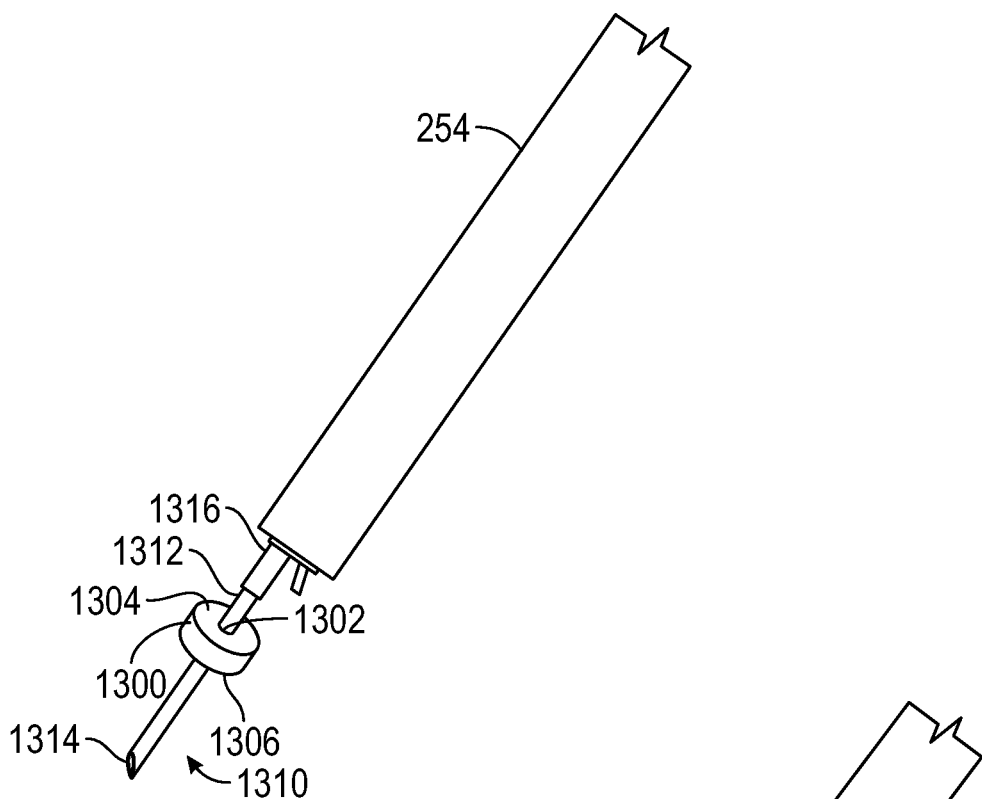
FIG. 13A is an isometric view of another exemplary injection needle, which may be used with the injection apparatus described herein, according to certain embodiments.
Figure 13B:
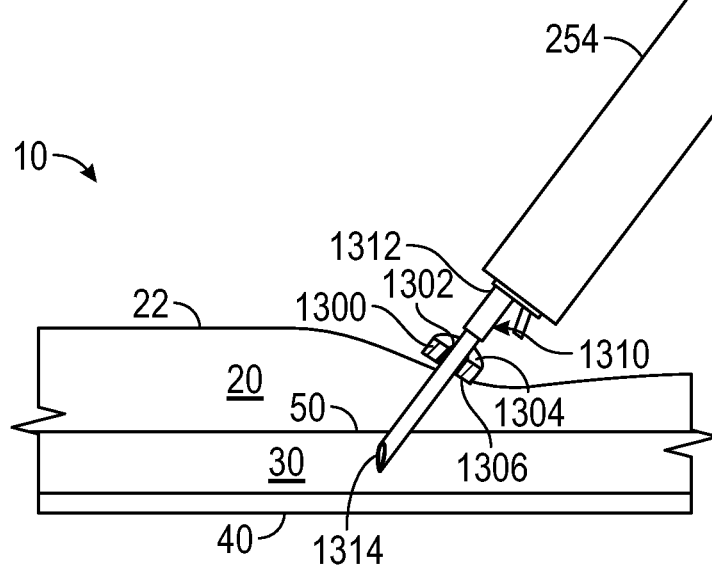
FIG. 13B is a side sectional view of the injection needle of FIG. 13A illustrating the injection needle inserted into the subretinal space, according to certain embodiments.

In some other embodiments illustrated in FIGS. 13A-13B, the depth of the injection needle 1310 is controlled by using an end stop 1300. In some other embodiments illustrated in FIGS. 14A-14B, the depth of the injection needle 1410 is controlled by using a curved injection needle 1410. Additional details regarding these embodiments are provided below.

At operation 406, the injection needle 110 is immobilized at the target position on the surface 22 of the retina 20 using a stabilizer 130. In certain embodiments illustrated in FIGS. 7A-7C, a pressure or fluid is applied through the lumen 128c of the multi-lumen tubing 120 to extend the stabilizer 130 beyond a distal end 122 of the lumen 128c to place the stabilizer 130 in contact with the surface 22 of the retina 20. The stabilizer 130 is configured to securely contact the retina 20 in such a way that the injection needle 110 is immobilized at the target position on the surface 22 of the retina 20. In certain embodiments, the stabilizer 130 is formed from a material which is conformal to the surface 22 of the retina 20 to increase the contact area therebetween.

Figure 8A:
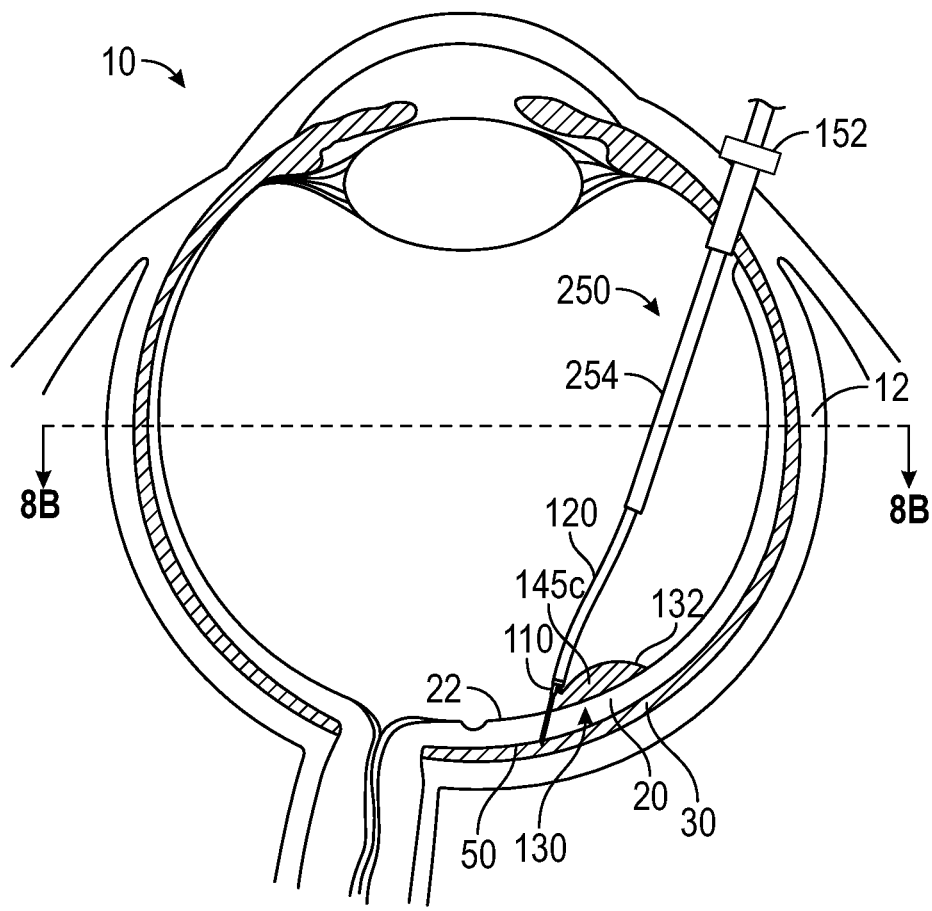
Figure 8B:
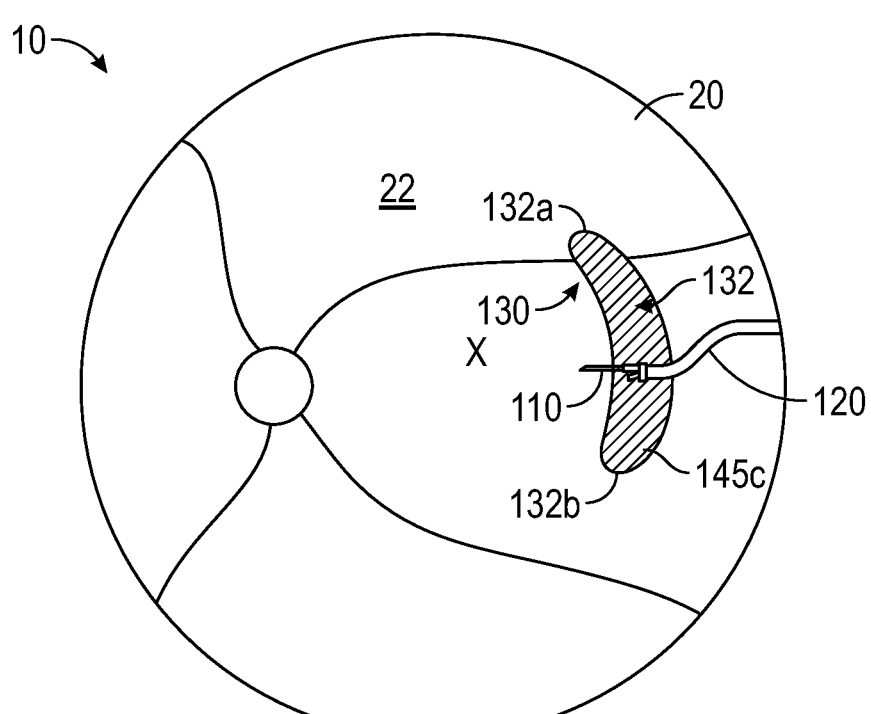

At operation 408, after the stabilizer 130 is in contact with the surface 22 of the retina 20, the cannula 254 of the inserter device 250 is retracted from the eye 10 (FIGS. 8A-8B). After the cannula 254 is retracted, the injection needle 110 and the multi-lumen tubing 120 are decoupled from external forces. As used herein, external forces generally include any forces applied to the injection needle 110 or the multi-lumen tubing 120 from outside the eye 10. For example, external forces generally include light and/or inadvertent movement of any part of the injection apparatus 100 by the surgeon or surgical assistant. In certain embodiments, the decoupling limits the effect of external forces associated with injection of the non-treatment solution 145a (operation 410) or injection of the treatment solution 145b (operation 412). In some other embodiments using a handheld injection instrument to manually control the injection in a two-step process, as described earlier, the decoupling limits the effect of external forces associated with movement of handheld instruments.

In certain embodiments illustrated in FIGS. 8A-8B, excess length of the multi-lumen tubing 120 is provided in an unconstrained state inside the eye 10 to facilitate decoupling. It will be appreciated that when external forces are applied to the multi-lumen tubing 120, the excess length enables movement of the multi-lumen tubing 120 inside the eye 10 without transfer of force to the injection needle 110. In some embodiments using the inserter device 260 of FIG. 2B, the inserter device 260 is decoupled from the multi-lumen tubing 120 after the retracting by sliding the multi-lumen tubing 120 through the slit 265.

Figure 9A:
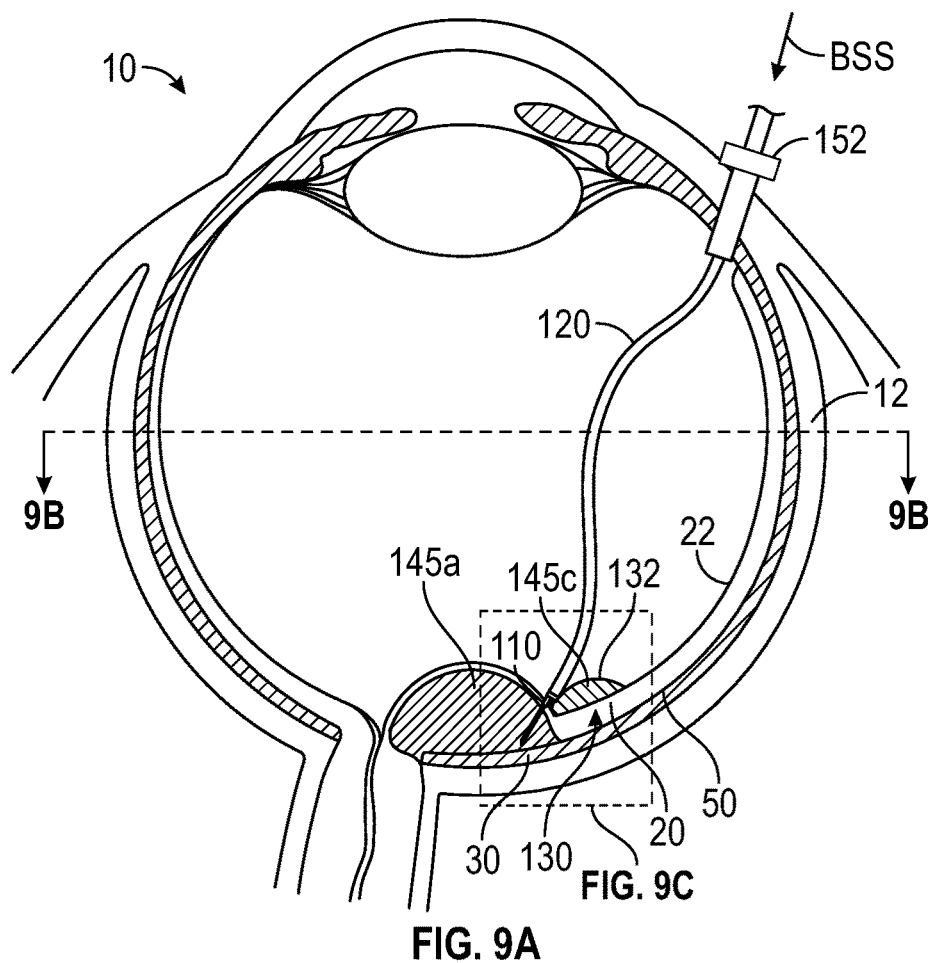
Figure 9B:
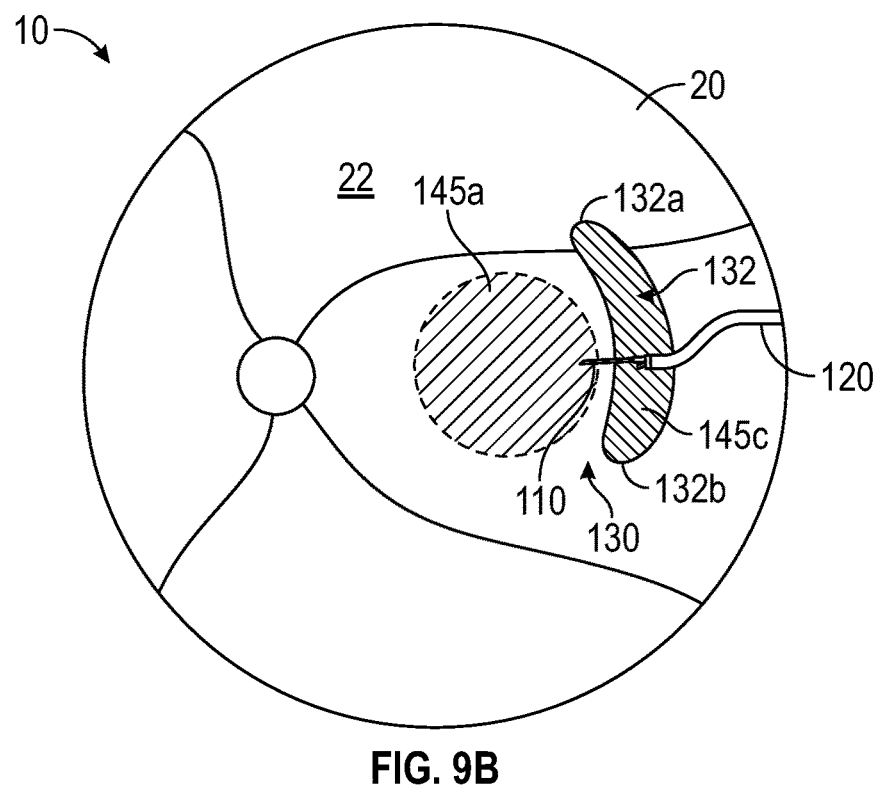
Figure 9C:
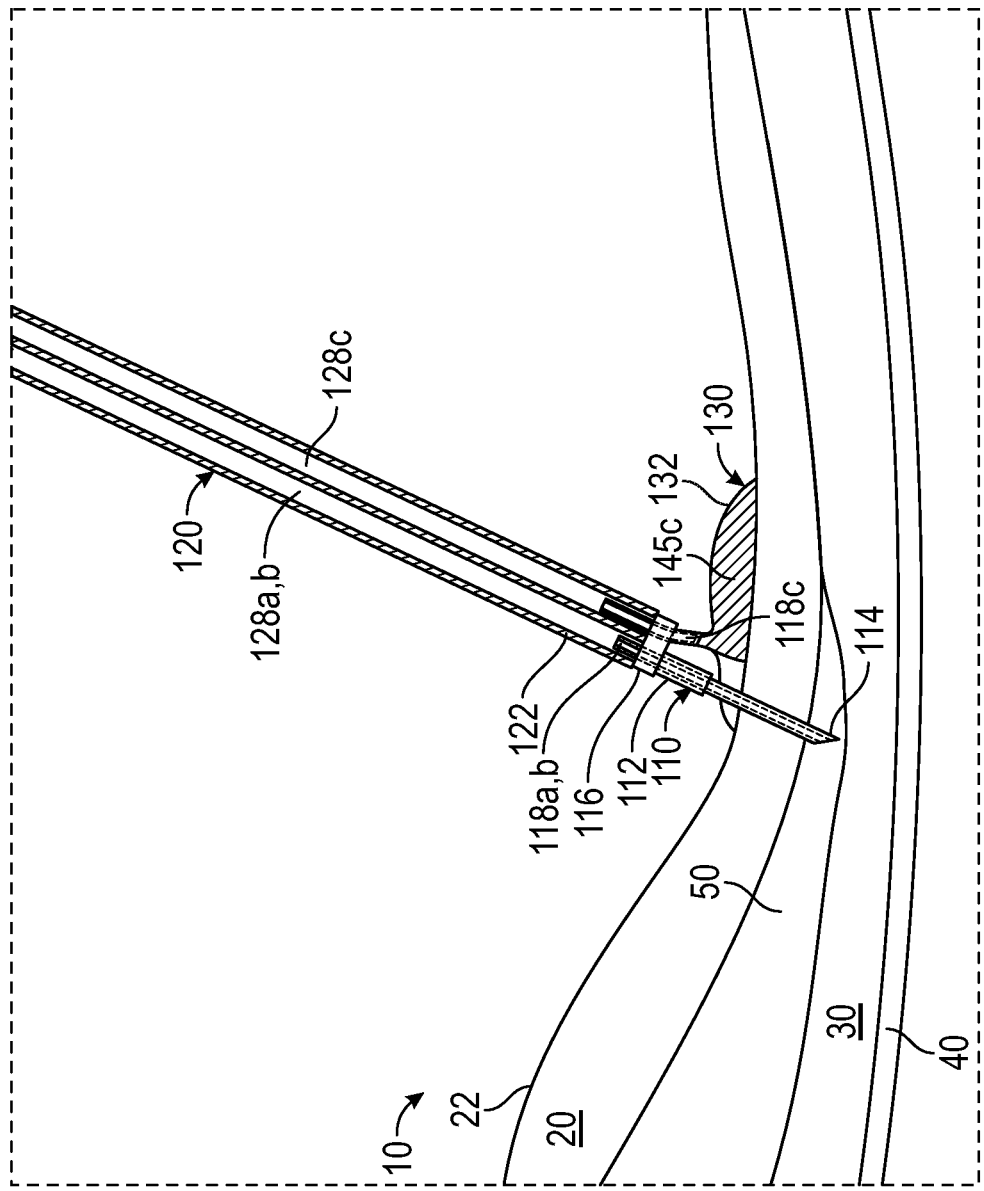
FIG. 9C is an enlarged sectional view of a portion of FIG. 9A illustrating formation of a bleb in the subretinal space, according to certain embodiments.

At operation 410, a non-treatment solution 145a is injected from the fluid control unit 140 to the subretinal space 50 via the lumen 128a of the multi-lumen tubing 120 (FIGS. 9A-9C). In some embodiments for example, the fluid pump 142 drives flow of the non-treatment solution 145a through the lumen 128a to inject the non-treatment solution 145a from the fluid reservoir 144a to the subretinal space 50. In certain embodiments, injection of the non-treatment solution 145a forms a bleb in the subretinal space 50 between the retina 20 and the RPE 30 (FIG. 9C). In certain embodiments, the bleb is a localized hemispherical lifting of the retina 20 which is visible through the surgical microscope. Thus, formation of the bleb by the non-treatment solution 145a provides visual confirmation that the distal end 114 of the injection needle 110 is disposed within the proper layer of the eye 10, namely in the subretinal space 50.

Figure 10A:
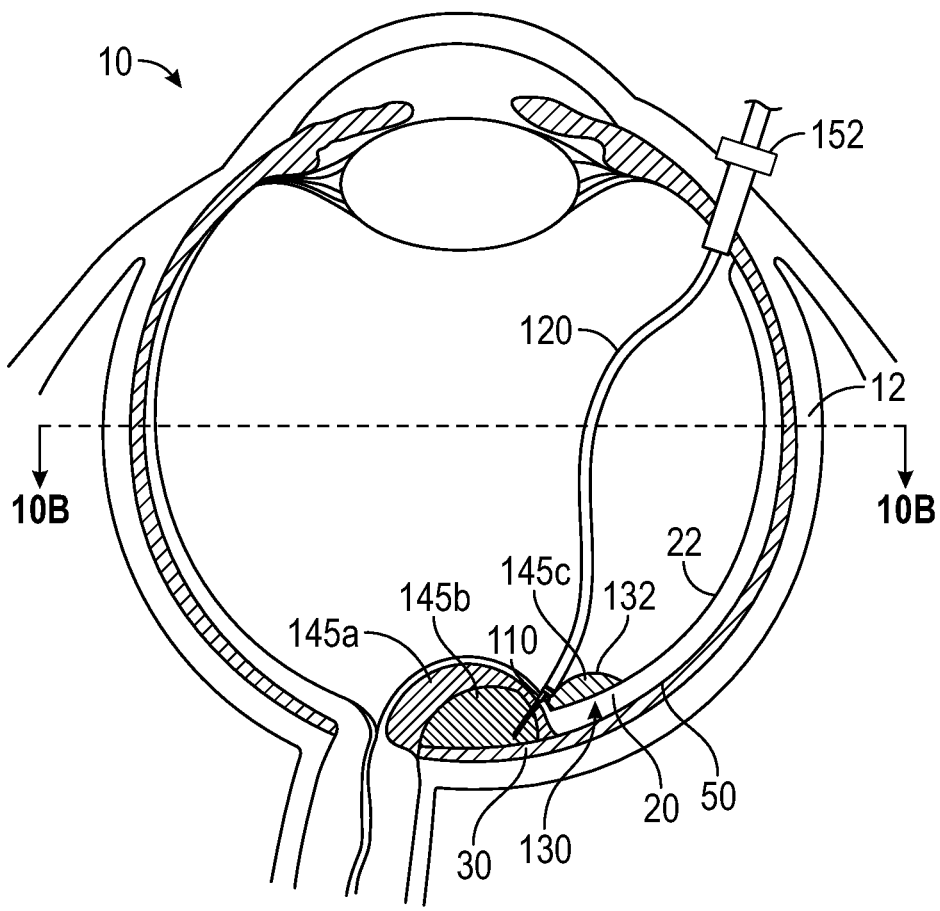
Figure 10B:
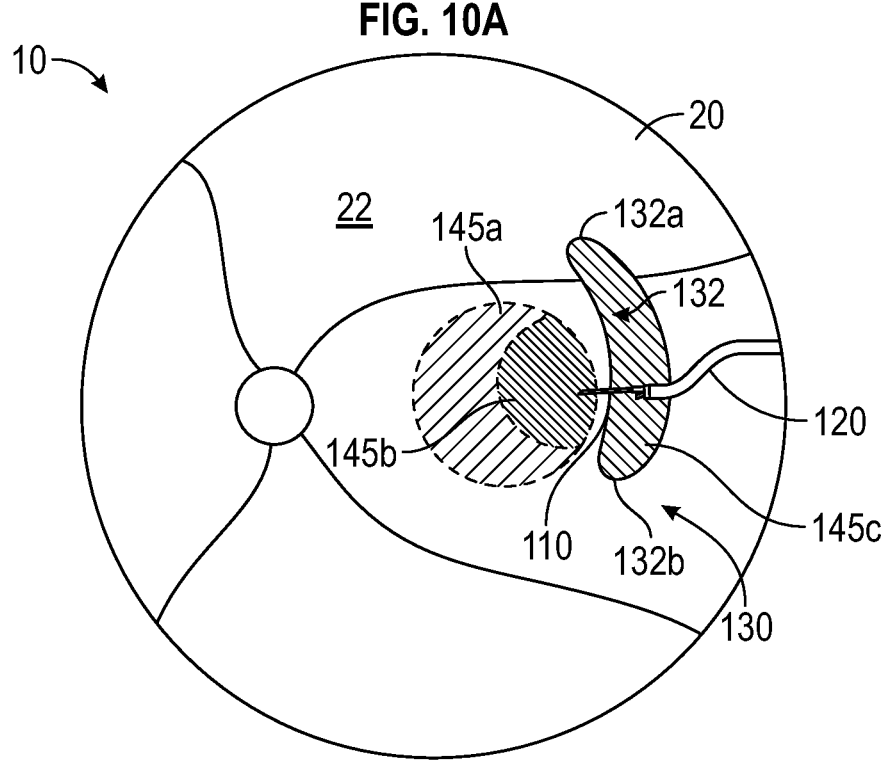
Figure 11A:
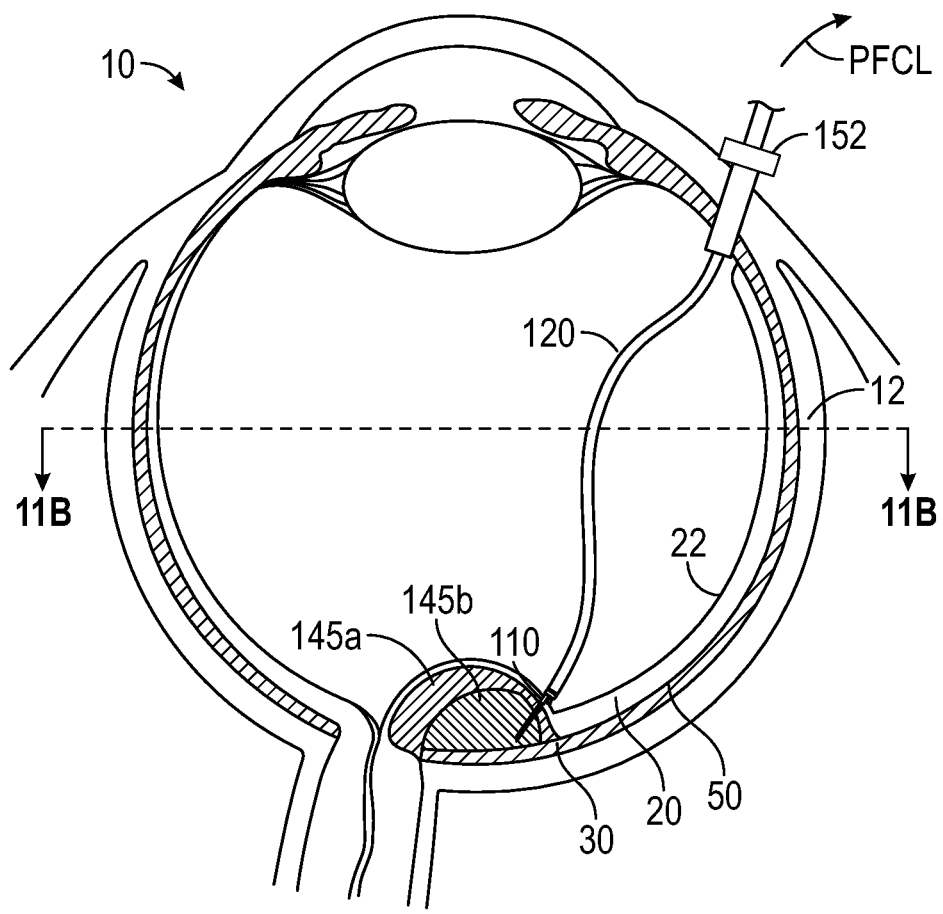
Figure 11B:
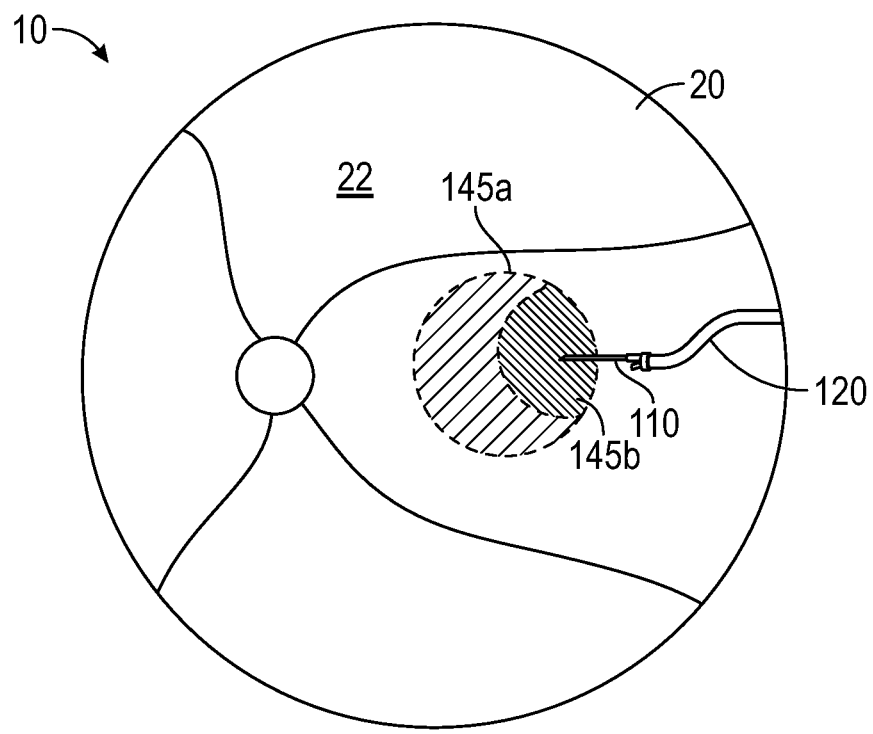

At operation 412, a treatment solution 145b is injected from the fluid control unit 140 to the subretinal space 50 via the lumen 128b of the multi-lumen tubing 120 (FIGS. 10A-10B). In certain embodiments, the fluid pump 142 drives flow of the treatment solution 145b through the lumen 128b to inject the treatment solution 145b from the fluid reservoir 144b to the subretinal space 50. In certain embodiments, injecting each of the non-treatment solution 145a and the treatment solution 145b is performed hands-free. In certain embodiments, the fluid pump 142 drives flow of each of the non-treatment solution 145a, the treatment solution 145b, and the working fluid 145c without manual actuation of the plurality fluid reservoirs 144a-c. In some embodiments, the fluid pump 142 operates according to instructions received from the controller 146. In some embodiments, the controller 146 receives control signals via the wireless receiver 147a. In certain embodiments, the surgeon or surgical assistant may control pressure or volume of injection of each of the plurality of fluids 145a-c using a foot pedal which is in wireless communication with the controller 146 via the wireless receiver 147a and the antenna 147b.

At operation 414, the injection needle 110 is remobilized by retracting the stabilizer 130 into the distal end 122 of the lumen 128c. Thus, the stabilizer 130 is removed from being in contact with the surface 22 of the retina 20. In certain embodiments, the working fluid 145c is removed from the lumen 128c using vacuum pressure to cause the stabilizer 130 to retract therein. In some embodiments, the stabilizer 130 is removed from being in contact with the surface 22 of the retina 20 without being retracted into the distal end 122 of the lumen 128c.

Figure 12A:
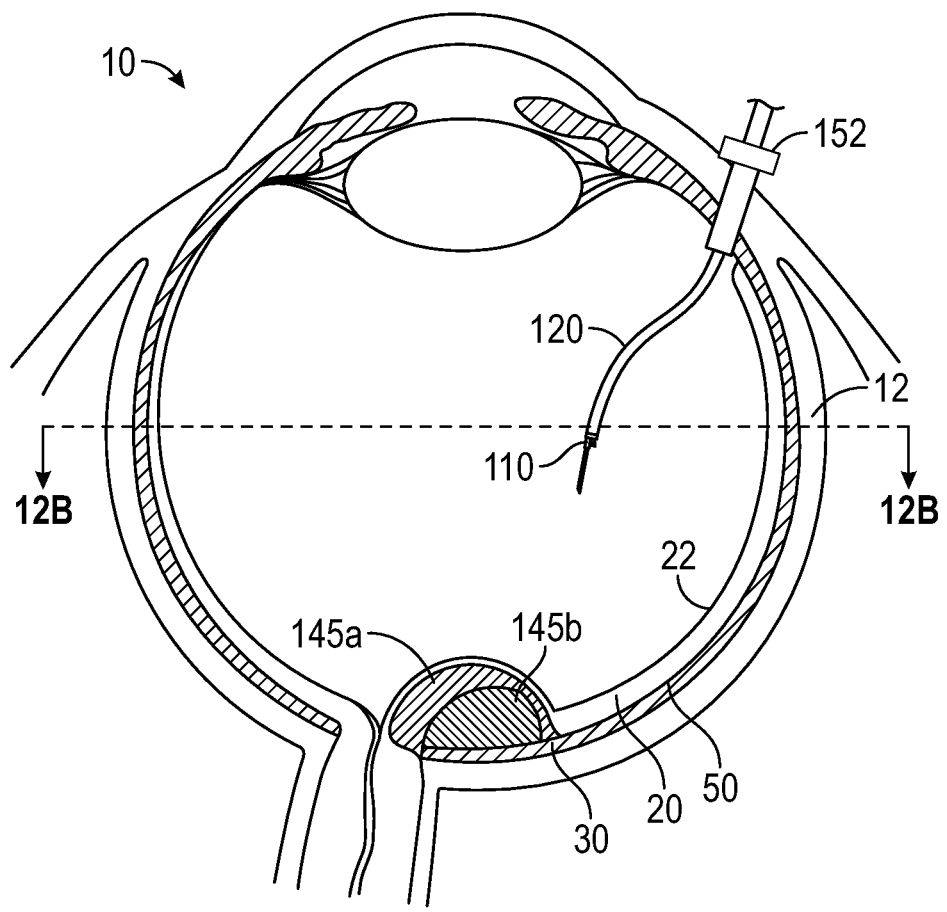
Figure 12B:
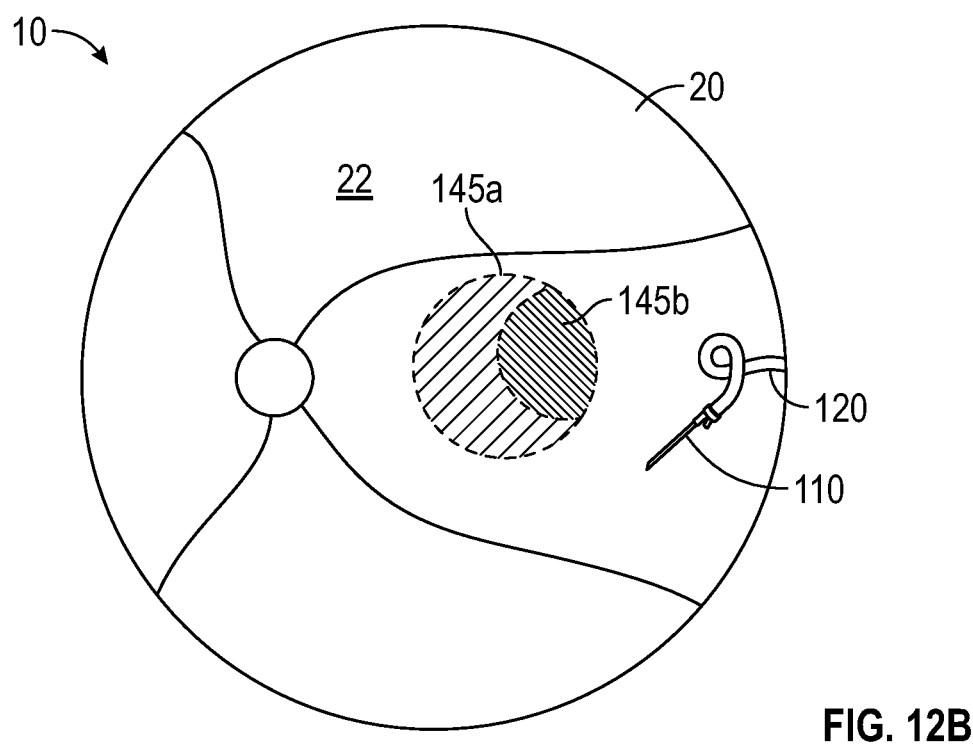

At operation 416, the multi-lumen tubing 120 and the injection needle 110 coupled thereto are removed from the eye 10 (FIGS. 12A-12B). Without the stabilizer 130 in contact with the retina 20, the injection needle 110 is able to be removed from within the subretinal space 50 by slight tension force applied to the multi-lumen tubing 120. In some embodiments, a retinal port formed by insertion of the injection needle 110 through the retina 20 may be relatively small compared to typical procedures owing to the various benefits of the apparatus and methods disclosed herein. In such embodiments, the retinal port may remain unpatched without issue. In some other embodiments, the retinal port may be filled with a sealing agent (e.g., fibrin glue, collagen, cyanoacrylate, cellular attachment factors, fibronectin, laminin, extracellular matrix-based hydrogels, polyacrylic acid, zinc polycarboxylate cement, silicone adhesive, or an ophthalmic viscosurgical device (OVD), or viscoelastic plug). In some other embodiments, the viscosity of the treatment solution 145b may be adequate to seal the retinal port.

Various alternative embodiments are described in detail below. It will be appreciated that the following embodiments may be combined with the injection apparatus 100 and method 400 without limitation. FIG. 13A is an isometric view of another exemplary injection needle 1310, which may be used with the injection apparatus 100 described herein. Referring to FIG. 13A, an end stop 1300 is disposed around the injection needle 1310 between the proximal end 1312 and the distal end 1314. In the embodiments of FIG. 13A, the end stop 1300 is an annular disk having a center bore 1302 for receiving the injection needle 1310 therethrough. The end stop 1300 has first and second opposing faces 1304, 1306 which are facing parallel to a longitudinal axis of the center bore 1302. In some other embodiments, the end stop 1300 may have a non-circular profile (e.g., a polygonal or oval profile). In some embodiments, the end stop 1300 has an inner diameter corresponding to an outer diameter of the injection needle 1310 to form an interference fit therebetween. In some other embodiments, the end stop 1300 may be integral with the injection needle 1310 or coupled to the injection needle 1310 by an adhesive or fastener.

FIG. 13B is a side sectional view of the injection needle 1310 of FIG. 13A illustrating the injection needle 1310 inserted into the subretinal space 50. The second face 1306 is in contact with the surface 22 of the retina 20 when the distal end 1314 of the injection needle 1310 is inserted into the subretinal space 50. The distance between the distal end 1314 and the second face 1306 is selected so that the distal end 1314 is correctly positioned between the retina 20 and the RPE 30 when the second face 1306 is in contact with the surface 22 of the retina 20. Therefore, the end stop 1300 prevents the injection needle 1310 from being inserted too far into the eye 10 (e.g., through the RPE 30 or the Bruch's membrane 40), which can damage the eye 10. In some other embodiments, the second face 1306 is tapered to facilitate insertion of the end stop 1300 through the sclera.

Figure 14A:
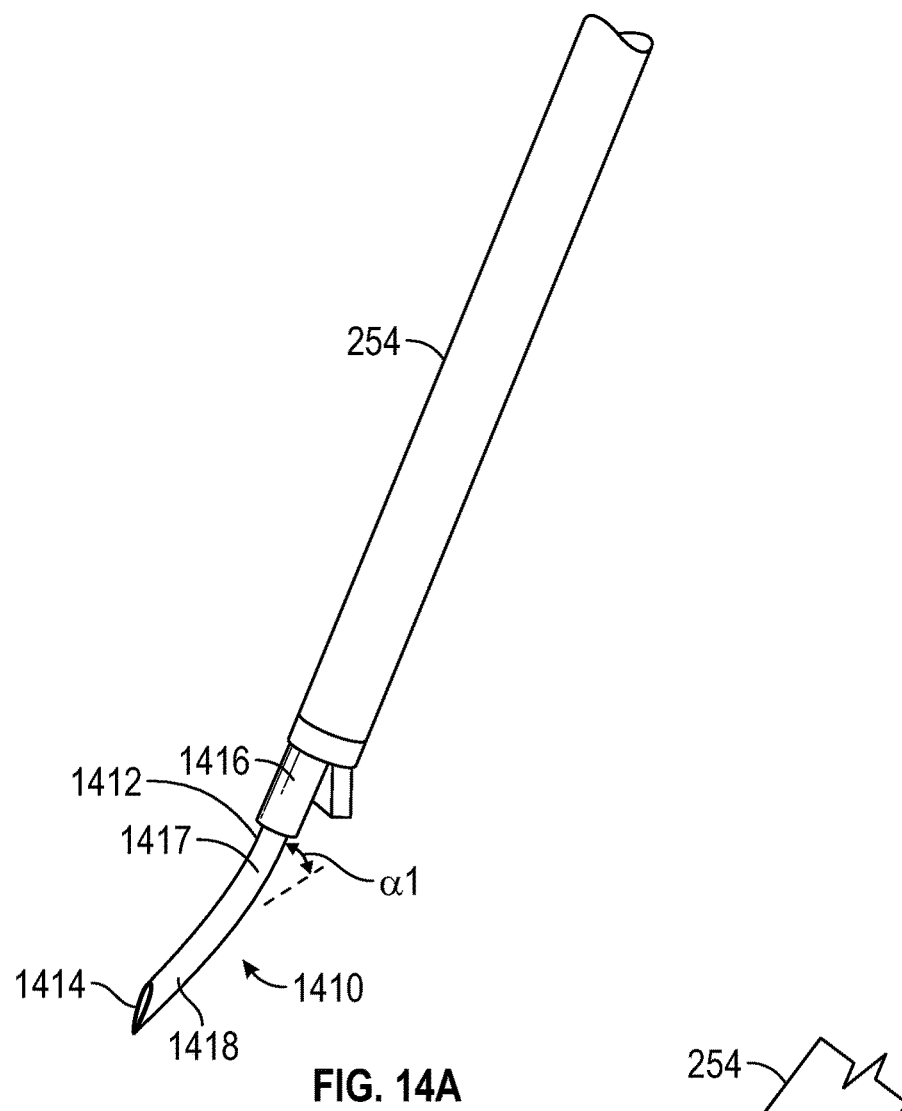
FIG. 14A is an isometric view of yet another exemplary injection needle, which may be used with the injection apparatus described herein, according to certain embodiments.

FIG. 14A is an isometric view of yet another exemplary injection needle 1410, which may be used with the injection apparatus 100 described herein. Referring to FIG. 14A, the injection needle 1410 is curved. For example, in certain embodiments, the injection needle 1410 has a first portion 1417 extending substantially parallel to the center longitudinal axis 120x of the multi-lumen tubing 120 and a second portion 1418 extending at an angle α1 different from the first portion 1417. In certain embodiments, the angle α1 of the second portion 1418 is about 45 degrees or less (e.g., about 30 degrees or less or from about 10 degrees to about 30 degrees).

Figure 14B:
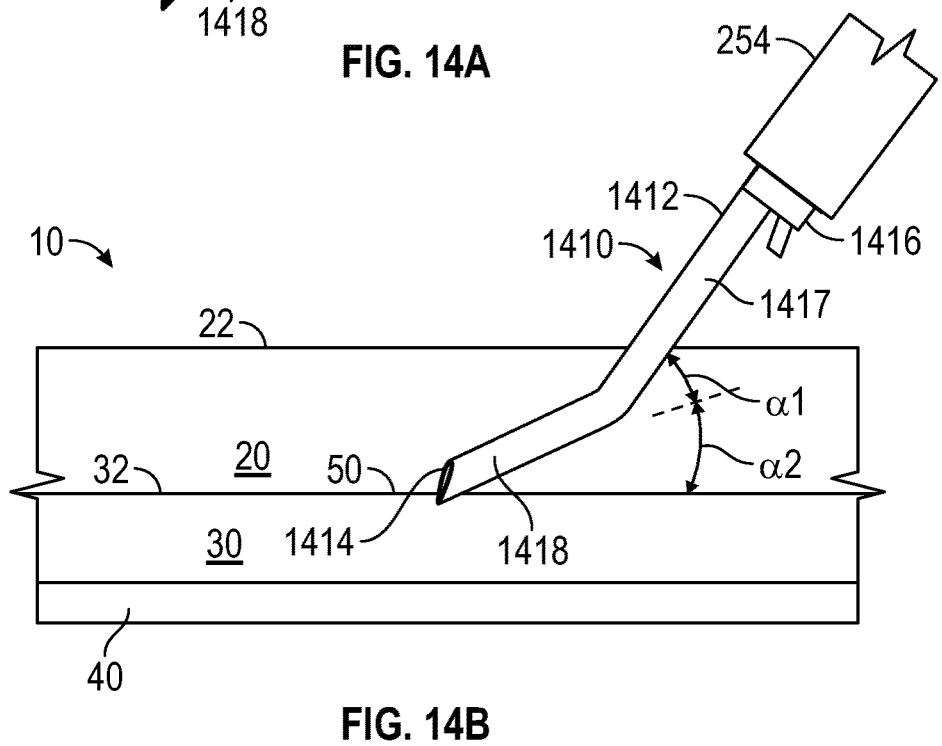
FIG. 14B is a side sectional view of the injection needle of FIG. 14A illustrating the injection needle inserted into the subretinal space, according to certain embodiments.

FIG. 14B is a side sectional view of the injection needle 1410 of FIG. 14A illustrating the injection needle 1410 inserted into the subretinal space 50. Referring to FIG. 14B, an angle α2 between the second portion 1418 of the injection needle 1410 and the surface 32 of the RPE 30 is less than an angle (α1+α2) between the first portion 1417 and the surface 32. Because of the angle α2 of the second portion 1418, the injection needle 1410 enters the subretinal space 50 at a shallower angle than the angle (α1+α2) between the first portion 1417 and the surface 32. For example, compare the lower entry angle α2 of the curved injection needle 1410 (FIG. 14B) to the relatively higher entry angle of the straight injection needle 1310 (FIG. 13B). Beneficially, the curve of the injection needle 1410 helps correctly position the distal end 1414 between the retina 20 and the RPE 30, thereby helping prevent the injection needle 1410 from being inserted too far into the eye 10 (e.g., through the RPE 30 or the Bruch's membrane 40).

Figure 15:
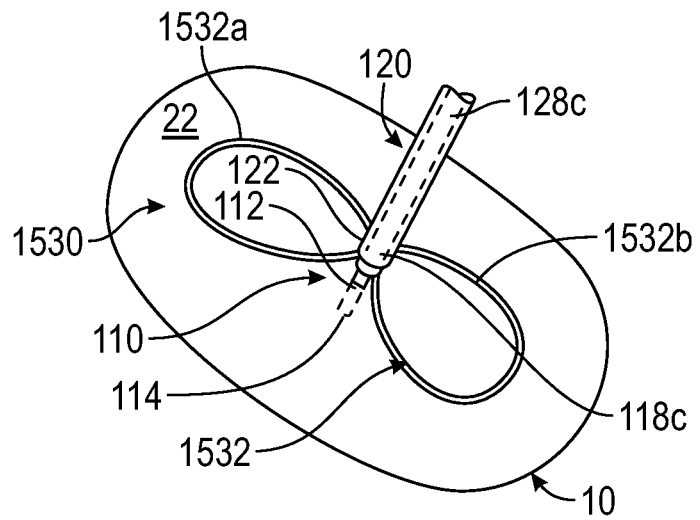
FIG. 15 is a top isometric view of another exemplary stabilizer, which may be used with the injection apparatus described herein, according to certain embodiments.

FIG. 15 is a top isometric view of another exemplary stabilizer 1530, which may be used with the injection apparatus 100 described herein. In the embodiments of FIG. 15, the stabilizer 1530 is shown in the extended position. In the retracted position, the stabilizer 1530 may be disposed within the port 118c of the connector piece 116 and/or disposed inside the lumen 128c of the multi-lumen tubing 120. Referring to FIG. 15, the stabilizer 1530 is a wire 1532 formed from a shape memory alloy or a material having a high degree of elasticity (e.g., nitinol). The wire 1532 is coupled to the connector piece 116 of the injection needle 110. In certain embodiments illustrated in FIG. 15, the wire 1532 is formed into a pair of wings 1532a, 1532b. In some other embodiments, the wire 1532 can be formed into any suitable shape including without limitation, round, oval, or polygonal. In the retracted position, the wire 1532 is disposed within the port 118c of the connector piece 116 and/or within the lumen 128c such that the wings 1532a, 1532b are folded generally parallel to the center longitudinal axis 120x of the multi-lumen tubing 120. In some embodiments, a working fluid 145c (e.g., PFCL) is injected from the fluid reservoir 144c of the fluid control unit 140 (FIG. 1A) through the lumen 128c to apply a pressure to extend the wire 1532 from the lumen 128c. In the extended position, the wings 1532a, 1532b may extend substantially along an axis perpendicular to the center longitudinal axis 120x of the multi-lumen tubing 120. In some embodiments, the wire 1532 is held in place primarily due to frictional forces between the wire 1532 and the surface 22 of the retina 20. In some embodiments, in the extended position, the wire 1532 has a flattened profile. For example, in some embodiments, a width of the wire 1532 measured parallel to the surface 22 of the retina 20 is greater (e.g. at least 2× greater, at least 5× greater, or at least 10× greater) than a height of the wire 1532 measured orthogonal to the surface 22.

Figure 16:
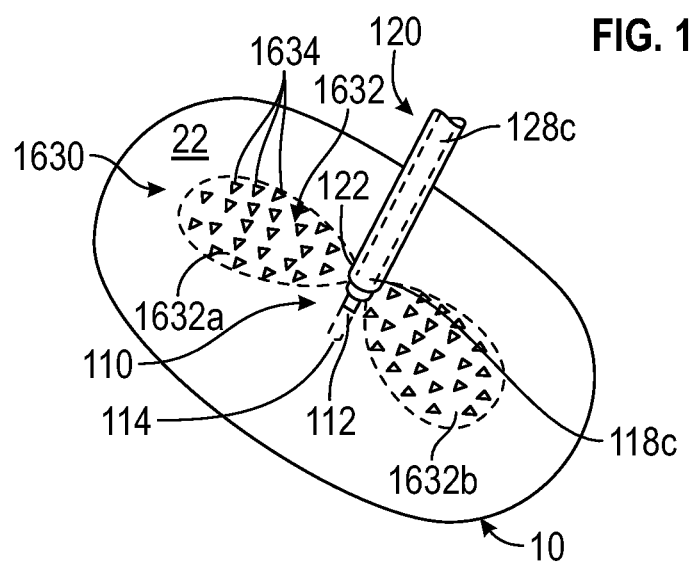
FIG. 16 is a top isometric view of yet another exemplary stabilizer, which may be used with the injection apparatus described herein, according to certain embodiments.

FIG. 16 is a top isometric view of yet another exemplary stabilizer 1630, which may be used with the injection apparatus 100 described herein. In the embodiments of FIG. 16, the stabilizer 1630 is shown in the extended position. In the retracted position, the stabilizer 1630 may be disposed within the port 118c of the connector piece 116 and/or disposed inside the lumen 128c of the multi-lumen tubing 120. In certain embodiments illustrated in FIG. 16, which can be combined with other embodiments disclosed herein without limitation, the stabilizer 1630 includes a plurality of barbs 1634 disposed on a structure 1632 (e.g., a balloon, a wire, a plate, or combinations thereof). The structure 1632 is shown in phantom to more clearly illustrate the barbs 1634 disposed on an underside thereof. The barbs 1634 are configured to increase friction between the stabilizer 1630 and the surface 22 of the retina 20. In some other embodiments, other friction-inducing elements may be incorporated on the structure 1632 in addition to or as a substitute for the plurality of barbs 1634 (e.g., rough texture, teeth, spines, or combinations thereof). In certain embodiments illustrated in FIG. 16, the structure 1632 includes a pair of wings 1632a, 1632b. In some other embodiments, the structure 1632 can have any suitable shape including without limitation, round, oval, or polygonal. In some embodiments, in the extended position, the structure 1632 has a flattened profile. For example, in some embodiments, a width of the structure 1632 measured parallel to the surface 22 of the retina 20 is greater (e.g. at least 2× greater, at least 5× greater, or at least 10× greater) than a height of the structure 1632 measured orthogonal to the surface 22.

Figure 17:
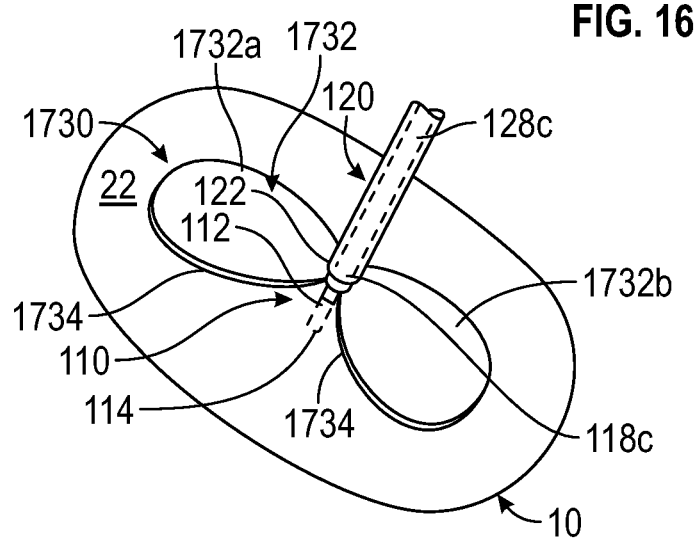
FIG. 17 is a top isometric view of yet another exemplary stabilizer, which may be used with the injection apparatus described herein, according to certain embodiments.

FIG. 17 is a top isometric view of yet another exemplary stabilizer 1730, which may be used with the injection apparatus 100 described herein. In the embodiments of FIG. 17, the stabilizer 1730 is shown in the extended position. In the retracted position, the stabilizer 1730 may be disposed within the port 118c of the connector piece 116 and/or disposed inside the lumen 128c of the multi-lumen tubing 120. Referring to FIG. 17, the stabilizer 1730 includes a plate 1732 and glue 1734. The plate 1732 may be formed from plastic, metal, polymer, nitinol, or combinations thereof. The glue 1734 can include an adhesive material based on at least one of fibrin, cyanoacrylates, gelatin, thrombin, polyethylene glycol, albumin, or glutaraldehyde. In some other embodiments, a non-adhesive material such as a viscoelastic material can be used for temporary physical bonding. In some other embodiments, the plate 1732 can have a profile which conforms to the surface 22 of the retina 20 and acts a suction cup to hold the plate 1732 in place. In some other embodiments, a vacuum pressure (e.g., from about 1 mmHg (millimeters of mercury) to about 650 mmHg) can be applied to a volume between the plate 1732 and the surface 22 of the retina 20.

In certain embodiments, the glue 1734 is pre-applied to the plate 1732 when the plate 1732 is folded inside the connector piece 116 (e.g., on an underside of the plate 1732 facing the surface 22 of the retina 20). In certain embodiments illustrated in FIG. 17, when the underside of the plate 1732 is in contact with the surface 22 of the retina 20, the glue 1734 is configured to at least lightly adhere the plate 1732 to the surface 22 of the retina 20. In some embodiments, the glue 1734 may increase friction between the plate 1732 and the surface 22 of the retina 20 without securing the surfaces together. In some other embodiments, the glue 1734 is applied via the lumen 128c in combination with the extension of the plate 1732. In some embodiments illustrated in FIG. 17, the plate 1732 includes a pair of wings 1732a, 1732b. In some other embodiments, the plate 1732 can have any suitable shape including without limitation, round, oval, or polygonal. In some embodiments, in the extended position, the plate 1732 has a flattened profile. For example, some embodiments, a width of the plate 1732 measured parallel to the surface 22 of the retina 20 is greater (e.g. at least 2× greater, at least 5× greater, or at least 10× greater) than a height of the plate 1732 measured orthogonal to the surface 22.

Figure 18:
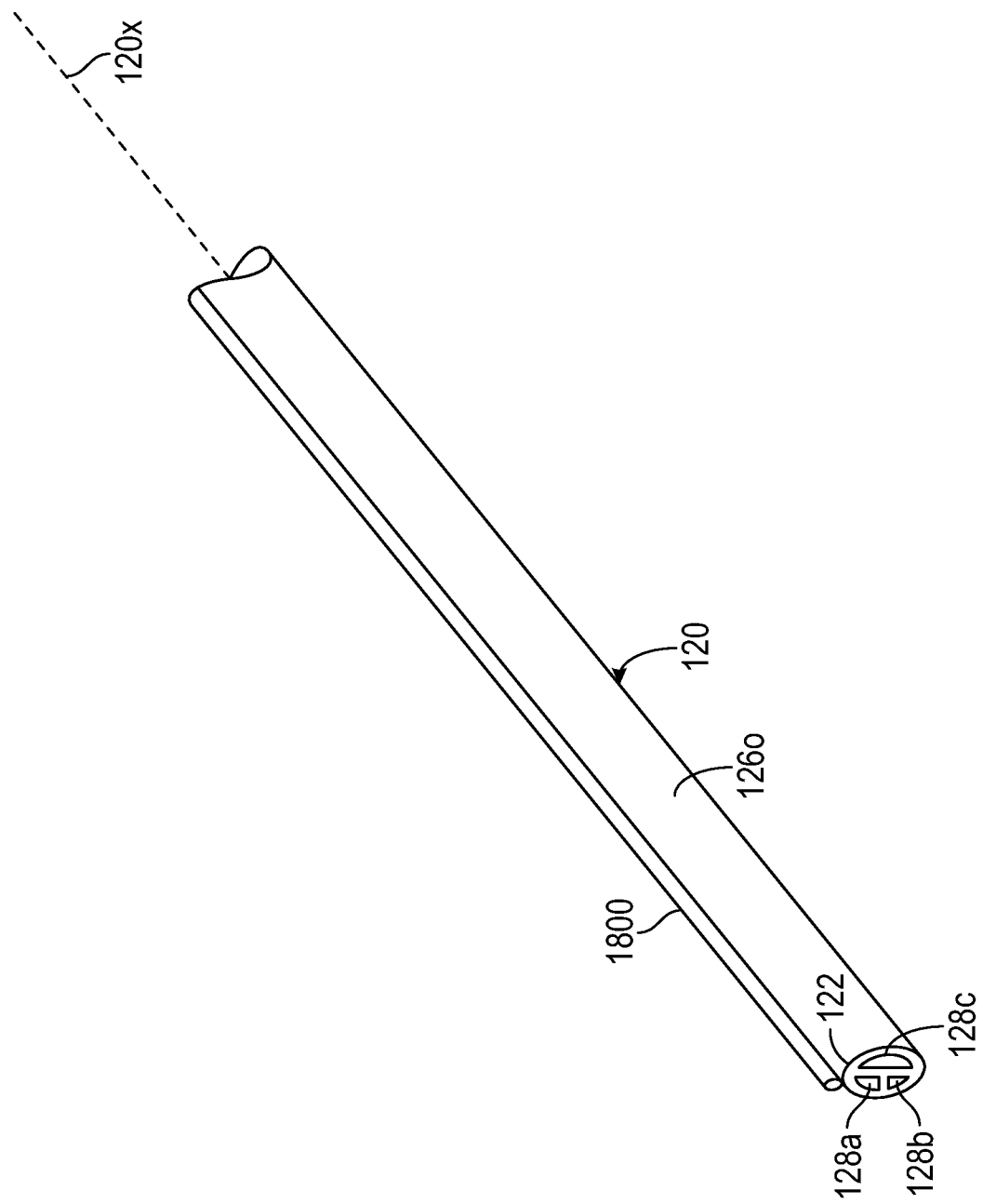
FIG. 18 is a schematic view of an exemplary guidewire, which may be used with the injection apparatus described herein, according to certain embodiments.

FIG. 18 is a schematic view of an exemplary guidewire 1800, which may be used with the injection apparatus 100 described herein. In certain embodiments, the guidewire 1800 is substituted in place of the inserter device 250. The guidewire 1800 is disposed along the outer wall 126o of the multi-lumen tubing 120 generally parallel to the center longitudinal axis 120x. In certain embodiments illustrated in FIG. 18, the guidewire 1800 extends to the distal end 122 of the multi-lumen tubing 120. In certain embodiments, the guidewire 1800 extends at least partially along the length of the multi-lumen tubing 120 including extending along a portion of the multi-lumen tubing 120 that is inserted into the eye 10. In some embodiments, the guidewire 1800 extends from the proximal end 124 to the distal end 122 of the multi-lumen tubing 120. The guidewire 1800 is more rigid than the multi-lumen tubing 120. The guidewire 1800 is configured to provide axial stiffness in the direction of the center longitudinal axis 120x in order to apply sufficient axial pressure to the injection needle 110 to insert the distal end 114 of the injection needle 110 into the subretinal space 50 at the target position on the surface 22 of the retina 20 without the use of the inserter device 250. The guidewire 1800 has a bending stiffness less than the axial stiffness in order to limit the transfer of undesirable bending forces from outside the eye 10 to the injection needle 110.

In some other embodiments where the inserter device 250 is not used, other mechanisms may be used to provide variable stiffness to the multi-lumen tubing 120. In certain embodiments, for example, the multi-lumen tubing 120 may have a higher stiffness during insertion of the distal end 114 of the injection needle 110 into the subretinal space 50 (operation 404) and a lower stiffness to decouple the injection needle 110 from external forces after the injection needle 110 is immobilized at the target position on the surface 22 of the retina 20 (operation 406) (e.g., during at least one of retraction of the cannula 254 (operation 408), injection of the non-treatment solution 145a (operation 410), or injection of the treatment solution 145b (operation 412)). In some embodiments, only a portion of the multi-lumen tubing 120 that is inserted into the eye 10 has variable stiffness. In some other embodiments, the entire length of the multi-lumen tubing 120 has variable stiffness.

In some other embodiments, application of electrical voltage to the multi-lumen tubing 120 changes the stiffness thereof. For example, at least a portion of the multi-lumen tubing 120 has a lower stiffness without the application of electrical voltage and a higher stiffness when electrical voltage is applied. In such embodiments, at least a portion of the multi-lumen tubing 120 may be formed form a material which undergoes a chemical or physical change induced by electrical voltage to impart greater stiffness to the multi-lumen tubing 120.

In some other embodiments, application of pneumatic pressure to the multi-lumen tubing 120 changes the stiffness thereof. For example, at least a portion of the multi-lumen tubing 120 has a lower stiffness without the application of pneumatic pressure and a greater stiffness when pneumatic pressure is applied. In such embodiments, one or more lumens of the multi-lumen tubing 120 may be filled with pneumatic pressure to increase the stiffness.

In some other embodiments, the multi-lumen tubing 120 may include a plurality of structural segments which impart a greater stiffness under compression and lower stiffness under tension. Thus, the multi-lumen tubing 120 may have a relatively greater stiffness when placed under compression during insertion of the distal end 114 of the injection needle 110 into the subretinal space 50 (operation 404). After the injection needle 110 is immobilized at the target position on the surface 22 of the retina 20 (operation 406), the multi-lumen tubing 120 may be placed under tension to induce a lower stiffness in order to decouple the injection needle 110 from external forces.

In summary, embodiments of the present disclosure improve the efficacy and safety of subretinal injection for treatment of ophthalmic conditions. In particular, embodiments of the present disclosure provide hands-free and precisely controlled fluid injection ensuring correct injection volume and dosing, proper flow velocity into the subretinal space without harming the retina or the RPE, and proper shear force in the needle to help maintain biologic activity of various therapeutics carried by the injection fluid. Furthermore, embodiments of the present disclosure decouple the injection needle from external forces preventing inadvertent movement of the injection needle which can cause tearing of the retina. Furthermore, embodiments of the present disclosure provide two injection steps, i.e., injection of a non-treatment solution and a treatment solution, without removing the injection needle from the subretinal space mitigating damage to the retina caused by re-entry of the injection needle.

While the foregoing is directed to embodiments of the present disclosure, other and further embodiments of the disclosure may be devised without departing from the basic scope thereof, and the scope thereof is determined by the claims that follow.

Example Embodiments

Embodiment 1: The apparatus of claim 1, wherein the injection needle and the multi-lumen tubing are configured to be decoupled from external forces after the injection needle is immobilized at the position on the surface of the retina.

Embodiment 2: The apparatus of claim 9, wherein the stabilizer comprises nitinol wire, wherein the nitinol wire is extended by applying pressure or fluid thereto, and wherein, in the extended position, the nitinol wire has first and second wings extending substantially along an axis perpendicular to a longitudinal axis of the distal end of the multi-lumen tubing.

Embodiment 3: The apparatus of claim 9, wherein the stabilizer comprises barbs configured to increase friction between the stabilizer and the surface of the retina.

Embodiment 4: The apparatus of claim 9, wherein the stabilizer comprises glue and a plate, wherein the glue is disposed on a surface of the plate, and wherein, when the surface of the plate is in contact with the surface of the retina, the glue is configured to increase friction therebetween.

Embodiment 5: The method of claim 15, further comprising decoupling the inserter device from the multi-lumen tubing after the retracting.

What is claimed is:

1. An apparatus for performing a subretinal injection into a subretinal space between a retina and a retinal pigment epithelium of an eye, the apparatus comprising:
   an injection needle having a proximal end and a distal end, the distal end configured to be insertable into the subretinal space at a position on a surface of the retina;
   a multi-lumen tubing having a distal end coupled to the proximal end of the injection needle and a proximal end coupled to a fluid control unit, the multi-lumen tubing having a first lumen and a second lumen;
   a stabilizer configured to immobilize the injection needle at the position on the surface of the retina; and
   the fluid control unit having a first fluid reservoir containing a non-treatment solution and a second fluid reservoir containing a treatment solution, wherein the fluid control unit is configured to inject the non-treatment solution from the first fluid reservoir to the subretinal space via the first lumen, and wherein the fluid control unit is configured to inject the treatment solution from the second fluid reservoir into the subretinal space via the second lumen;
   wherein the stabilizer comprises a balloon, wherein the balloon is extended by filling with a liquid, and wherein, in the extended position, the balloon has first and second wings extending substantially along an axis perpendicular to a longitudinal axis of the distal end of the multi-lumen tubing;

wherein the balloon has a flattened profile such that a width of the balloon measured parallel to the surface of the retina is at least two times greater than a height of the balloon measured orthogonal to the surface of the retina; and wherein the multi-lumen tubing further comprises a third lumen, wherein the stabilizer is coupled to a distal end of the third lumen, and wherein fluid applied through the third lumen is configured to extend the stabilizer beyond the distal end of the third lumen thereby placing the stabilizer on the surface of the retina.

2. The apparatus of claim 1, wherein the fluid control unit further comprises a third fluid reservoir, and wherein the fluid control unit is configured to inject a working fluid from the third fluid reservoir via the third lumen to extend the stabilizer.

3. The apparatus of claim 1, wherein the fluid control unit further comprises a pump configured to drive flow of each of the non-treatment and treatment solutions, the pump being at least one of a variable volume control pump, a syringe pump, a peristaltic pump, a venturi pump, a lever-actuated pump, a valve-actuated pump, or combinations thereof.

4. The apparatus of claim 1, wherein the fluid control unit is attachable to at least one of a surgical microscope or a patient forehead.

5. The apparatus of claim 1, further comprising an inserter device, wherein the multi-lumen tubing is disposed through the inserter device.

6. The apparatus of claim 5, wherein the inserter device comprises a slit extending longitudinally from a proximal end to a distal end thereof, and wherein the inserter device is configured to be decoupled from the multi-lumen tubing outside the eye by sliding the multi-lumen tubing through the slit.

7. The apparatus of claim 5, wherein the inserter device comprises an enclosed bore extending longitudinally from a proximal end to a distal end thereof, and wherein the inserter device is configured to remain coupled to the multi-lumen tubing outside the eye.

\* \* \* \* \*